United States Patent
Santore et al.

(10) Patent No.: US 11,091,789 B2
(45) Date of Patent: *Aug. 17, 2021

(54) SENSORS AND METHODS FOR CAPTURE, KILLING, AND RELEASE OF BACTERIA

(71) Applicant: THE UNIVERSITY OF MASSACHUSETTS, Boston, MA (US)

(72) Inventors: Maria Santore, Sunderland, MA (US); Bing Fang, Amherst, MA (US)

(73) Assignee: THE UNIVERSITY OF MASSACHUSETTS, Boston, MA (US)

( * ) Notice: Subject to any disclaimer, the term of this patent is extended or adjusted under 35 U.S.C. 154(b) by 169 days.

This patent is subject to a terminal disclaimer.

(21) Appl. No.: 15/886,327

(22) Filed: Feb. 1, 2018

(65) Prior Publication Data

US 2018/0171378 A1 Jun. 21, 2018

Related U.S. Application Data

(63) Continuation of application No. 14/501,503, filed on Sep. 30, 2014, now Pat. No. 9,920,353.

(60) Provisional application No. 61/884,206, filed on Sep. 30, 2013.

(51) Int. Cl.
*C12Q 1/24* (2006.01)
*G01N 33/543* (2006.01)
*A61L 2/238* (2006.01)

(52) U.S. Cl.
CPC ......... *C12Q 1/24* (2013.01); *G01N 33/54346* (2013.01); *A61L 2/238* (2013.01)

(58) Field of Classification Search
CPC ...... G01N 33/54346; C12Q 1/24; A61L 2/238
See application file for complete search history.

(56) References Cited

U.S. PATENT DOCUMENTS

| | | |
|---|---|---|
| 2010/0009379 A1 | 1/2010 | Santore et al. |
| 2015/0093774 A1 | 4/2015 | Santore et al. |

OTHER PUBLICATIONS

Fang et al.; "Antimicrobial surfaces containing cationic nanoparticles: How immobilized, clustered, and protruding cationic charge presentation affects killing activity and kinetics"; Colloids and Surfaces B: Biointerfaces, vol. 125; 2015; pp. 255-263.

Fang et al.; "Bacterial Adhesion on Hybrid Cationic Nanoparticle-Polymer Brush Surfaces: Ionic Strength Tunes Capture From Monovalent to Multivalent Binding"; Colloids and Surfaces B: Biointerfaces, vol. 87; 2011; pp. 109-115.

Fang et al.; "Using Flow to Switch the Valency of Bacterial Capture on Engineered Surfaces Containing Immobilized Nanoparticles"; Langmuir, vol. 28; 2012; pp. 7803-7810.

Gon et al.; "How Bacteria Adhere to Brushy PEG Surfaces: Clinging to Flaws and Compressing the Brush"; Macromolecules, vol. 45; 2012; pp. 8373-8381.

Gon et al.; "Interaction of Cationic Proteins and Polypeptides with Biocompatible Cationically-Anchored PEG Brushes"; Macromolecules, vol. 44; 2011; pp. 8161-8168.

Gon et al.; "Manipulating Protein Adsorption using a Patchy Protein-Resistant Brush"; Langmuir, vol. 26, No. 14; 2010; pp. 12147-12154.

Gon et al.; "Sensitivity of Protein Adsorption to Architectural Variations in a Protein-Resistant Polymer Brush Containing Engineered Nanoscale Adhesive Sites"; Langmuir, vol. 27; 2011; pp. 15083-15091.

Gon et al.; "Single Component and Selective Competitive Protein Adsorption in a Patchy Polymer Brush: Opposition Between Steric Repulsions and Electrostatic Attractions"; Langmuir, vol. 27, No. 4; 2011; pp. 1487-1493.

Holmes et al.; "Surface-modified nanoparticles as a new, versatile, and mechanically robust nonadhesive coating: Suppression of protein adsorption and bacterial adhesion"; Journal of Biomedical Materials Research Part A, vol. 91A; 2009; pp. 824-833.

Huang et al.; "Poly(L-lysine)-g-poly(ethylene glycol) Layers on Metal Oxide Surfaces: Surface-Analytical Characterization and Resistance to Serum and Fibrinogen Adsorption"; Langmuir, vol. 17; 2001; pp. 489-498.

Kenausis et al.; "Poly(L-lysine)-g-Poly(ethylene glycol) Layers on Metal Oxide Surfaces: Attachment Mechanism and Effects of Polymer Architecture on Resistance to Protein Adsorption"; J. Phys. Chem. B, vol. 104; 2000; pp. 3298-3309.

Pogodin et al.; "Biophysical Model of Bacterial Cell Interactions with Nanopatterned Cicada Wing Surfaces"; Biophysical Journal, vol. 104; 2013; pp. 835-840.

Srivastava et al.; "Integrated Magnetic Bionanocomposites Through Nanoparticle-Mediated Assembly of Ferritin"; J. Am. Chem. Soc, vol. 129; 2007; pp. 11776-11780.

Zhang et al.; "Manipulating Microparticles with Single Surface-Immobilized Nanoparticles"; Langmuir, vol. 24; 2008; pp. 6404-6408.

*Primary Examiner* — Satyendra K Singh
(74) *Attorney, Agent, or Firm* — Cantor Colburn LLP

(57) ABSTRACT

There is provided a renewable sensor for sensing or selectively capturing a targeted bacteria in a fluid. The renewable sensor includes a surface, the surface includes a substrate, a biologically or bacterially non-adhesive feature disposed on or in functional proximity to at least a portion of the substrate; and an adhesive elements disposed on or in functional proximity to the non-adhesive feature, a flow channel in operative contact with the surface; and a detector configured to detect the targeted cell type captured on the surface. Also provided are method for using the sensor and the surface.

56 Claims, 19 Drawing Sheets

FIG. 1.
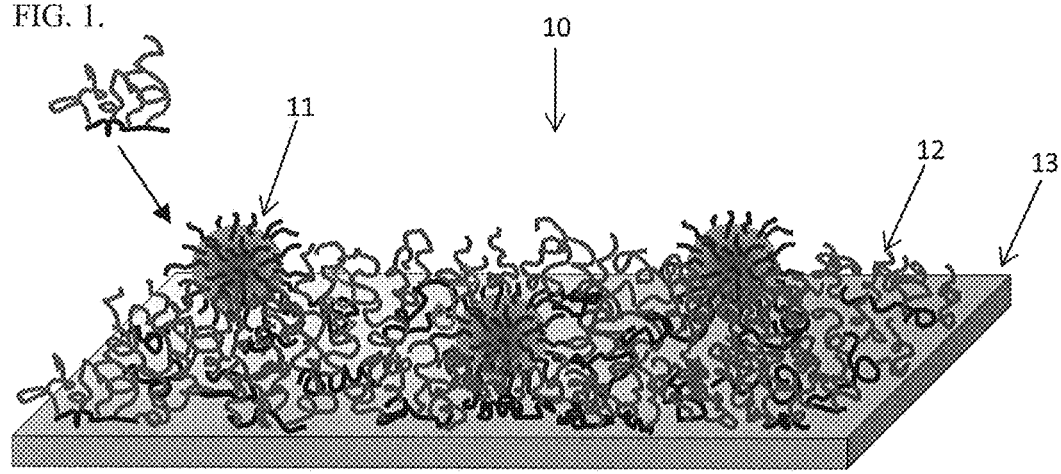
FIGS. 3A and 3B
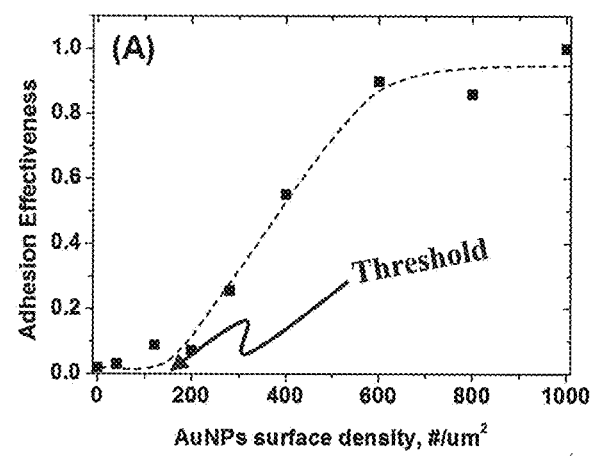
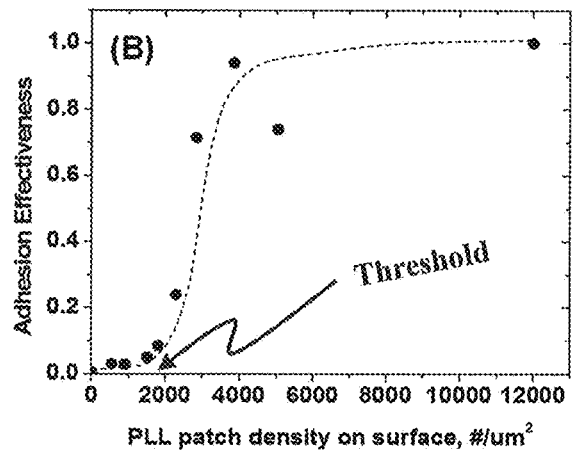

FIG. 13

| Bacteria Concentration | Appearance | | Viability Image |
|---|---|---|---|
| | Initial | 4 hours | Live/ Dead Stain on drop of suspension |
| $10^5$ cells/ml<br>$1.6 \times 10^9$ np avail /cell<br>$1.5 \times 10^7$ np adh'd/orig cell | 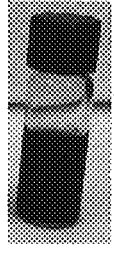 |  | 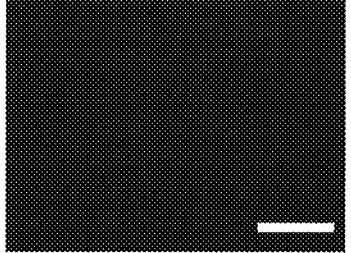 |
| $10^6$ cells/ml<br>$1.6 \times 10^8$ np avail /cell<br>$1.5 \times 10^7$ np adh'd/orig cell | 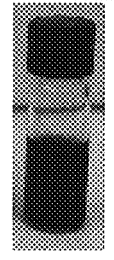 | 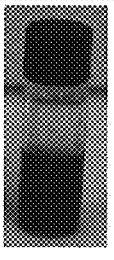 | 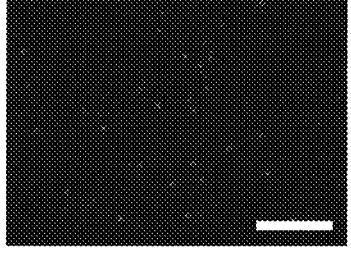 |
| $10^7$ cells/ml<br>$1.6 \times 10^7$ np avail /cell<br>$1.5 \times 10^7$ np adh'd/orig cell | 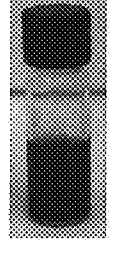 | 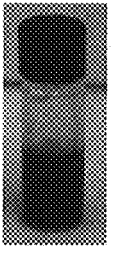 | 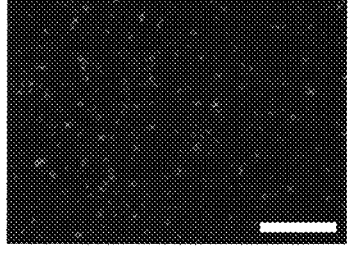 |
| $10^8$ cells/ml<br>$1.6 \times 10^6$ np avail /cell<br>$1.6 \times 10^6$ np adh'd/orig cell | 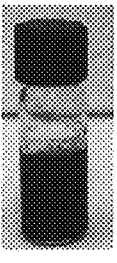 |  | 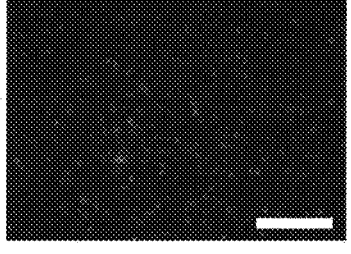 |

The scale bars are 50 μm.

SENSORS AND METHODS FOR CAPTURE, KILLING, AND RELEASE OF BACTERIA

CROSS-REFERENCE TO RELATED APPLICATION

This application is a Continuation of U.S. application Ser. No. 14/501,503, filed on Sep. 30, 2014, which claims the benefit of U.S. Provisional Application Ser. No. 61/884,206, filed Sep. 30, 2013, which is incorporated by reference herein in its entirety.

STATEMENT OF FEDERALLY SPONSORED RESEARCH

This invention was made with U.S. Government support under Grant Numbers DMR-08-05061, DMR-0820506, and CMMI-1025020, all of which were awarded by the National Science Foundation (NSF). The U.S. Government has certain rights in this invention.

COLOR DRAWINGS STATEMENT

The patent or application file contains at least one drawing executed in color. Copies of this patent or patent application publication with color drawing(s) will be provided by the Office upon request and payment of the necessary fee.

TECHNICAL FIELD

This application relates to sensors and methods for the capture of bacteria, and in particular to methods for the capture and release of bacteria using renewable surfaces, capture and killing of bacteria, and capture, killing, and release of bacteria using renewable surfaces, as well as selective capture of bacteria.

BACKGROUND

Adhesion of bacteria to a surface, or "capture," is used in a variety of applications, for example in purification devices or bacterial sensors. Selective bacteria capture is particularly useful in sensors, for example. Subsequent release of the bacteria is useful in online bacterial sensors where after a positive sensing event, the bacteria are released from the surface, and the renewed surface can be used to continue sensing. Such sensors can be operated continuously. In some applications, killing of the bacteria before release is desirable. For example, surfaces that kill bacteria on contact are desirable for biomedical devices and surfaces in public spaces. Prior art surfaces typically must balance killing functionality with ease of the release of bacteria in order to provide nonfouling surfaces and regeneration, which has not been successfully achieved. Accordingly, prior art methods often require substantial chemical processes to remove the bacteria and regenerate their adhesive surfaces. Easy removal of the captured bacteria (living or dead) would be especially useful to avoid fouling of the surfaces.

There accordingly remains a need for methods for bacteria capture with the capacity to release and/or kill the bacteria. There is a particular need in the art for methods for bacteria capture and release using renewable surfaces, and for bacterial capture, kill, and release using renewable surfaces. There further remains a need in the art for improved methods for selective bacteria capture. The selectivity can be for bacteria in the presence of other biomolecules (e.g., proteins, carbohydrates, and the like), or in the presence of other cells, for example for specific bacterial strains.

SUMMARY

In an embodiment, a method of capturing and releasing bacteria from a surface comprises contacting a fluid comprising bacteria with the surface, wherein the surface comprises a biologically or bacterially nonadhesive feature disposed on or in functional proximity to at least a portion of a substrate; and adhesive elements disposed on or in functional proximity to the nonadhesive feature, under conditions effective to adhere at least a portion of the bacteria in the fluid to the surface; and releasing at least a portion of the adhered bacteria from the surface. The capture and release cycle can be repeated two or more times.

In another embodiment, a method of capturing and killing bacteria, the method comprises contacting a fluid comprising bacteria with a surface, wherein the surface comprises a biologically or bacterially nonadhesive feature disposed on or in functional proximity to at least a portion of a substrate; and adhesive elements disposed on or the nonadhesive feature, under conditions effective to adhere at least a portion of the bacteria in the fluid to the surface; and killing at least a portion of the adhered bacteria.

In still another embodiment, a method of capturing, killing, and releasing bacteria, the method comprises contacting a fluid comprising bacteria with a surface, wherein the surface comprises a biologically or bacterially nonadhesive feature disposed on or in functional proximity to at least a portion of a substrate; and adhesive elements disposed on or in functional proximity to the nonadhesive feature, under conditions effective to adhere at least a portion of the bacteria in the fluid to the surface; killing at least a portion of the adhered bacteria; and releasing at least a portion of the adhered bacteria from the surface. The capture, kill, and release cycle can be repeated two or more times. In an embodiment, the capture, kill, and release cycle is repeated four times.

A method of selectively capturing bacteria, the method comprising: contacting a fluid comprising bacteria and another biological component with a surface, wherein the surface comprises a bacterially nonadhesive feature disposed on at least a portion of the substrate, wherein the feature is further nonadhesive to the biological component; and bacterially adhesive elements disposed on the substrate and contacting the nonadhesive feature, under conditions effective to selectively adhere at least a portion of the bacteria in the fluid to the surface. The capture and release cycle can be repeated two or more times.

In yet another embodiment, a renewable sensor for sensing or selectively capturing a targeted bacteria in a fluid, the sensor comprising a surface comprising a substrate, a biologically or bacterially non-adhesive feature disposed on or in functional proximity to at least a portion of the substrate; and an adhesive elements disposed on or in functional proximity to the non-adhesive feature, a flow channel in operative contact with the surface; and a detector configured to detect the targeted cell type captured on the surface. The bacteria captured on the adhesive element can be released thereby renewing or regenerating the sensor. In one embodiment, the captured bacteria are released by exposing the adhesive element to a flow-rate fluid exceeding that occurring during bacterial adhesion. In another embodiment, the captured bacteria are released by introducing air bubbles.

Due to the renewable nature, the sensor is suitable for application in online or continuous sensing.

The above described and other features are exemplified by the following figures and detailed description.

BRIEF DESCRIPTION OF THE FIGURES

The patent or application file contains at least one drawing executed in color. Copies of this patent or patent application publication with color drawing(s) will be provided by the Office upon request and payment of the necessary fee.

The following Figures are exemplary embodiments, which do not limit the claims.

FIG. 1 is a schematic diagram of an embodiment of a surface having adhesive elements embedded in a biologically or bacterially nonadhesive layer. The adhesive elements 11 are functionalized gold nanoparticles that protrude forward from nonadhesive feature 12.

FIGS. 2A-2D are schematic diagrams of four surfaces, with darker shade indicating areas of cationic charge and lighter shade indicating a nonadhesive feature (e.g., polyethylene glycol, PEG brush), in which FIG. 2A shows a saturated layer of poly-l-lysine;

FIG. 2B shows a dense layer of cationically-functionalized nanoparticles backfilled with a polymer (e.g., PEG brush); FIG. 2C shows a sparse layer of poly-l-lysine coils backfilled with a polymer (e.g., polyethylene glycol brush); and FIG. 2D shows a sparse layer of nanoparticles backfilled with a polymer (e.g., PEG brush);

FIG. 3A is a graph of adhesion efficiency versus surface density (#/μm$^2$) of cationically-functionalized nanoparticles.

FIG. 3B is a graph of is a graph of adhesion efficiency versus PLL surface density (#/μm$^2$) showing the adhesion efficiency of S. Aureus PLL-containing surfaces from buffer, with a Debye length of 2 nm.

FIG. 5A is for a surface having 400 nanoparticles/μm$^2$ embedded in a 2 kiloDalton PEG brush, and FIG. 5B is for a surface having 3500 poly-l-lysine patches (20 kiloDalton)/μm$^2$, embedded in a 2 kiloDalton brush.

FIG. 6A shows the results for a surface containing 400 nanoparticles per micron squared, while FIG. 6B shows the results for a surface containing 3500 PLL coils per micron squared as indicated on the figures. The areas around the nanoparticles or PLL coils on the two surfaces are backfilled with a polyethylene glycol polymer brush.

FIGS. 9B to 9D illustrates incubation and challenge at different Debye lengths, wherein FIG. 9B relates to 1 nm Debye length, FIG. 9C relates to 2 nm Debye length, and FIG. 9D relates to 4 nm Debye length). Surfaces used for each run contain 3500 poly-l-lysine patches/μm$^2$.

FIG. 13 shows appearances of mixtures of nanoparticles and bacterial cells in buffers at various concentrations and various time intervals. FIG. 13 also shows viability images of mixtures of nanoparticles and bacterial cells obtained applying live/dead stain to drop of each suspension. The red color dots indicates dead bacteria, while green color dots indicate living bacteria.

FIGS. 16A and 16B relate to a first run of bacterial capture and release. FIGS. 16C and 16D relate to a second run of bacterial capture and release. FIGS. 16E and 16F relate to a third run of bacterial capture and release. FIGS. 16G and 16H relate to a fourth run of bacterial capture and release. Panel A shows the surface prior to bacterial exposure and includes imperfections on the camera lens which appear in subsequent frames. Panels B, D, F, and H show the surface after each of 4 sequential bacteria exposures. Panels C, E, and G show the surface after sequential bacteria-releasing steps.

DETAILED DESCRIPTION

Figures 2A, 2B, 2C, 2D:
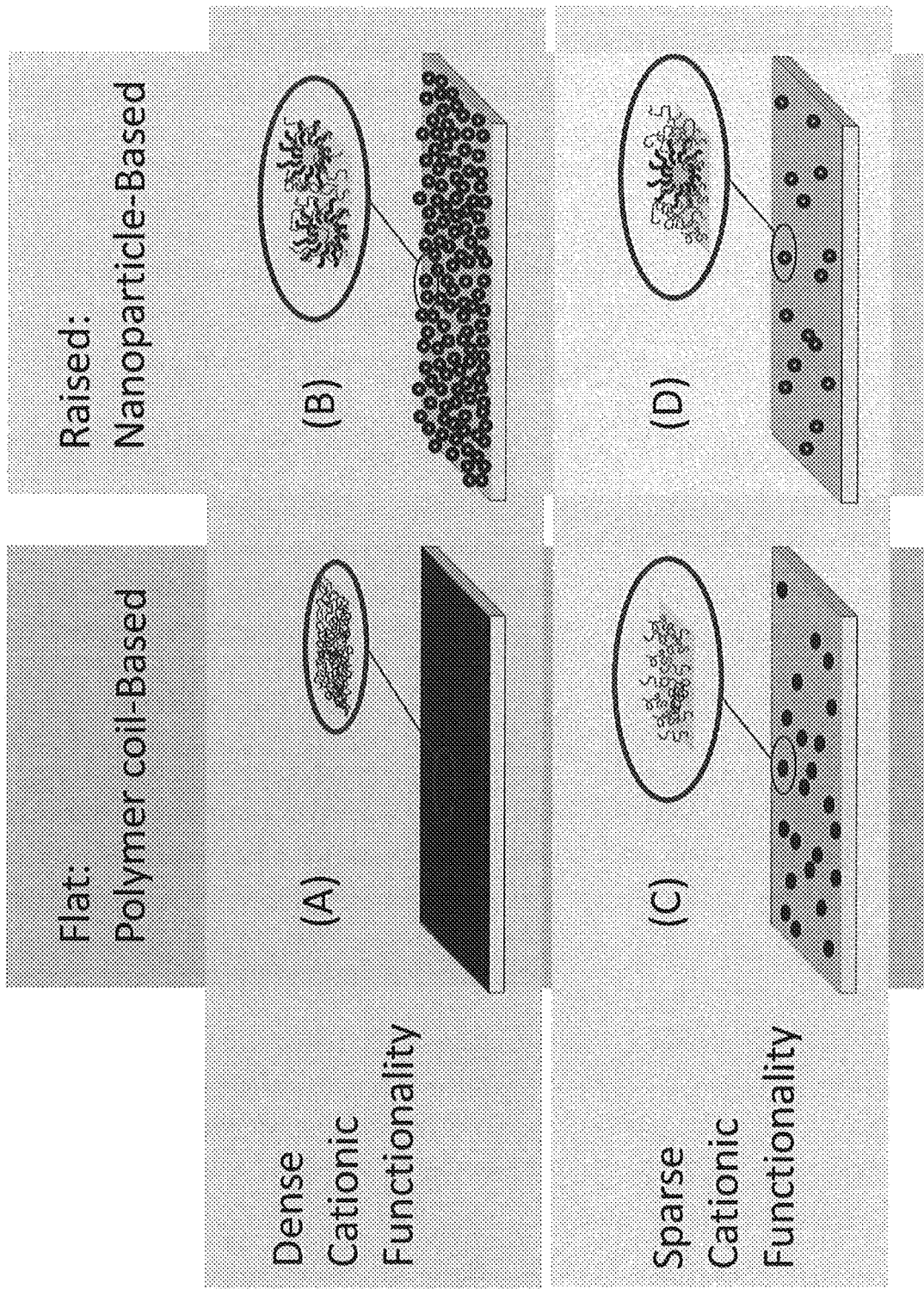

Disclosed herein are methods for bacteria capture and release; bacteria capture and kill; bacterial capture, kill, and release; and selective bacteria capture. A common feature of the method is use of a surface having a biologically or bacterially nonadhesive feature. Discrete adhesive "elements" or localized regions of functionality are disposed on the substrate, proximal to or contacting the nonadhesive surface functionality. The inventors have found that discretization of the adhesive functionality into nano-scale surface elements allows the adhesion and killing functionality to be compatible with bacteria release. Thus, upon exposure to bacteria, the bacteria can be captured, then killed and/or released, depending on the appropriate selection of the nonadhesive feature, the adhesive elements, their physical arrangement, and the conditions under which the bacteria contact the surface. In an especially useful feature, the bacteria capture/kill/release or capture/release or cycle can be repeated multiple times using the same surface. It is also possible to selectively capture the bacteria using the surfaces. The methods are useful in a wide variety of devices where bacteria capture is desirable, for example biomedical devices, purification devices, textiles, and sensors.

In an embodiment, there is provided a method of capturing and releasing bacteria from a surface, the method comprises contacting a fluid comprising bacteria with the surface, wherein the surface comprises a biologically or bacterially nonadhesive feature disposed on or in functional proximity to at least a portion of a substrate; and adhesive elements disposed on or in functional proximity to the nonadhesive feature, under conditions effective to adhere at least a portion of the bacteria in the fluid to the surface; and releasing at least a portion of the adhered bacteria from the surface. In another embodiment, the method further comprises, after release of the adhered bacteria, re-contacting the surface with a fluid comprising bacteria under conditions effective to adhere at least a portion of the bacteria to the surface; and releasing at least a portion of the bacteria from the surface. In some embodiments, the steps of re-contacting the surface with a fluid comprising bacteria and releasing at least a portion of the bacteria from the surface are sequentially repeated at least three times without significant loss of adhesive ability of the adhesive elements. The step of releasing at least a portion of the adhered bacteria can be carried out by exposing the adhesive elements to the fluid flowing at a rate higher than the flow-rate required under conditions effective to adhere the bacteria to the surface. The step of releasing at least a portion of the adhered bacteria can be carried out by exposing the adhesive elements to air bubbles. In an embodiment, the step of releasing at least a portion of the adhered bacteria removes substantially all of the adhered bacteria. In an embodiment, the step of releasing at least a portion of the adhered bacteria is carried out by exposing the adhesive elements to a shear rate of about 100 to about 3000 s⁻¹. Within the range of 100 to 3000 s¹, the shear rate may be suitably selected from about 200 to 2800 s⁻¹, 400 to 2500 s⁻¹, 800 to 2000 s⁻¹, and 900 to 1800 s⁻¹. In one embodiment, the shear rate is 1600 s⁻¹. The step of releasing at least a portion of the adhered bacteria can release bacteria that have been adhered to the surface for 20 minutes or more.

In an embodiment, there is provided a method of capturing and killing bacteria. The method comprises contacting a fluid comprising bacteria with a surface, wherein the surface comprises a biologically or bacterially nonadhesive feature disposed on or in functional proximity to at least a portion of a substrate; and adhesive elements disposed on or the nonadhesive feature, under conditions effective to adhere at least a portion of the bacteria in the fluid to the surface; and killing at least a portion of the adhered bacteria. The biologically or bacterially nonadhesive feature can comprise a layer or region comprising a natural polymer, a protein, a synthetic polymer, a natural surfactant, a synthetic surfactant, a natural or a synthetic amphiphile, or a combination comprising at least one of the foregoing materials. In an embodiment, the synthetic polymer is a polyethylene glycol or polyethylene oxide. The adhesive elements can be randomly dispersed on the nonadhesive feature thereby forming discrete regions of adhesive functionality. In an embodiment, the adhesive elements comprise a cationically and/or hydrophobically-functionalized nanoparticles of gold. The nanoparticles of gold are not antimicrobial in free form. In an embodiment, the adhesive elements comprise about 100 to 2000 gold nanoparticles per square micrometer. Within the range of 100 to 2000, the gold particles can be present in an amount of about 150 to about 1800, about 200 to about 1600, about 250 to about 1400, about 300 to about 1000, or about 300 to about 600 nanoparticles per square micrometer. In an embodiment, the gold particles are present in an amount of about 400 nanoparticles per square micrometer. In another embodiment, the adhesive elements comprise poly-l-lysine having a molecular weight of about 10 to about 70 kiloDaltons. Within the range of 10 to 70 kiloDaltons, the molecular weight can be about 10 to about 60 kiloDaltons, about 15 to about 50 kiloDaltons, about 18 to about 40 kiloDaltons, and about 18 to about 30 kiloDaltons. The adhesive elements can comprise about 2000 to 20,000 poly-l-lysine units per square micrometer. Within the range of 2000 to 20,000, the amount can be about 2500 to about 10,000, about 3000 to about 6000, and about 3000 to about 4000 units per square micrometer. In an embodiment, the adhesive elements comprise 3500 poly-l-lysine units per square micrometer.

In an embodiment, the surface has a charge density of about $5\times10^{12}$ to about $50\times10^{12}$ cationic charges per $cm^2$. In an embodiment, the charge density is about $7\times10^{12}$ cationic charges per $cm^2$.

In an embodiment, there is provided a renewable sensor for sensing or selectively capturing a targeted bacteria in a fluid, the sensor comprises a surface comprising a substrate, a biologically or bacterially non-adhesive feature disposed on or in functional proximity to at least a portion of the substrate; and an adhesive elements disposed on or in functional proximity to the non-adhesive feature, a flow channel in operative contact with the surface; and a detector configured to detect the targeted cell type captured on the surface.

The substrate can comprise a glass, a synthetic polymer, a natural polymer, a metal, a metal oxide, a ceramic, or a combination comprising at least one of the foregoing materials. The substrate can be flat, contoured, a fiber, or a combination comprising at least one of the foregoing.

The biologically or bacterially nonadhesive feature can comprise a layer or region comprising a natural polymer, a protein, a synthetic polymer, a natural surfactant, a synthetic surfactant, a natural or a synthetic amphiphile, or a combination comprising at least one of the foregoing materials. In an embodiment, the protein or synthetic polymer is cross-linked, end-grafted, part of a copolymer, charged, neutral, zwitterionic, solvated, sterically repulsive, or a combination comprising at least one of the foregoing. The chains of the protein or synthetic polymer can be in their natural state, extended, in a random coil, folded, or partially extended. In an embodiment, the protein or synthetic polymer has a molecular weight of about 0.1 to about 500 kiloDaltons. Within the range of 0.1 to 500 kiloDaltons, the molecular weight can be about 0.2 to about 400 kiloDaltons, about 0.3 to about 300 kiloDaltons, about 0.5 to about 250 kiloDaltons, about 0.8 to about 200 kiloDaltons, about 1 to about 100 kiloDaltons, about 1.5 to about 50 kiloDaltons, about 1.5 to about 10 kiloDaltons. In an embodiment, the molecular weight is about 2 kiloDalton. In an embodiment, the synthetic polymer is a polyethylene glycol or polyethylene oxide.

The adhesive element can be a polypeptide, a protein, a hydrophobic synthetic polymer, a hydrophobic synthetic polymer particle, a cationic synthetic polymer, cationically-functionalized hydrophobic synthetic polymer, a cationically-functionalized hydrophobic synthetic polymer particle, a cationic dendrimer, a hydrophobic nanoparticle, a cationic nanoparticle, a cationically-functionalized nanoparticle, or combination comprising at least one of the foregoing. In an embodiment, the adhesive element can be a homopolypeptide comprising about 30 to about 500 structural units. In an embodiment, the adhesive element is poly-l-lysine having a molecular weight of about 10 to about 70 kiloDaltons. The adhesive element can be a cationically and/or hydrophobically functionalized nanoparticle comprising a metal, a metal oxide, or a ceramic core. In an embodiment, wherein the adhesive element is an amine-functionalized silica nanoparticle. The adhesive element can be a cationically and/or hydrophobically-functionalized metal nanoparticle of Groups 10 to 11 of the Periodic Table of the Elements. In an embodiment, the metal of the nanoparticle is gold. In an embodiment, the cationically and/or hydrophobically-functionalized nanoparticle comprises a gold core having an average diameter of about 2 to about 20 nanometers and having about 30 to about 2000 ligands disposed thereon. The ligands can comprise 1-mercaptoundecane and/or N,N,N,-trimethyl(11-mercaptoundecyl)ammonium chloride.

The adhesive elements can be present on the substrate surface at a spatial density of about 1 element per square micrometer to about 50,000 elements per square micrometer. In an embodiment, the adhesive elements are present on the substrate surface at a spatial density of about 5 elements per square micrometer to about 2000 elements per square micrometer.

The substrate surface can be a component of a biomedical device, a purification device, a textile, or a sensor.

FIG. 1 is a schematic representation of a surface having discretized adhesive functionality. Surface 10 includes a biologically or bacterially nonadhesive feature 12 disposed on or in functional proximity to a surface of substrate 13. The biologically or bacterially nonadhesive feature 12 can be a surface layer as shown, a discrete component, a region, or a functionality. The biologically or bacterially nonadhesive feature 12 can be a continuous surface layer or functionality on the substrate surface. Alternatively, a biologically or bacterially nonadhesive component, region, or functionality can be discontinuous on the substrate surface, provided that the nonadhesive component, region, or functionality is of sufficient size to allow exposure of the bacteria to both the nonadhesive component, region, or functionality and the adhesive elements. Discrete adhesive elements 11 are in functional proximity with the nonadhesive feature 12. In an embodiment, adhesive elements 11 are in functional proximity to the biologically or bacterially nonadhesive features 12 (not shown). In another embodiment, the adhesive elements are disposed on and in contact with a nonadhesive feature, for example a surface layer 12 as shown. For example, the adhesive elements 11 can be on and in contact with the outer surface of the nonadhesive feature; or the adhesive elements can be embedded in the nonadhesive feature, for example surface layer 12 as shown, or the component, region, or functionality 12. The adhesive elements 11 can protrude from the nonadhesive feature 12 as shown, or be even with or embedded within the nonadhesive feature 12. For example, the adhesive elements can protrude up to about 100 nm from the nonadhesive feature 12. The adhesive elements 11 can be distributed randomly, in a pattern, or a combination thereof with respect to the substrate.

The substrate can be of any material compatible with the intended use of the method, for example a glass, a synthetic polymer, a natural polymer, a metal, a metal oxide, a ceramic, or a combination comprising at least one of the foregoing materials. The substrate can further be of any shape or configuration compatible with the intended use of the methods, for example flat, contoured, a fiber, or a combination comprising at least one of the foregoing shapes. For example, the substrate can be a glass configured as part of a sensor, or a flexible polymer that can be attached to an element of a purification unit or a biomedical device.

The biologically or bacterially nonadhesive feature is compatible with the intended use of the method, nonadhesive to biological agents and/or bacteria, and compatible with the adhesive elements. The nonadhesive feature can be disposed on and in contact with the substrate, or intermediate layers can be present to provide desired functionality such as enhanced adhesion to the substrate. The nonadhesive feature can be physically or chemically bonded to the substrate. As stated above, the nonadhesive feature can be continuous or discontinuous on the substrate. The nonadhesive feature can be flat and conformal to the surface of the substrate (e.g., a flat layer disposed concentrically on a fiber substrate), or contoured (e.g., a layer or other shape thicker in some regions than in other regions).

A wide variety of materials can be used as the nonadhesive surface layer, for example certain surfactants, amphiphiles, and polymers, either synthetic or naturally occurring, for example certain natural polymers such as cellulosics including hydroxyethyl cellulose or pullulan, or synthetic polymers, particularly hydrophilic synthetic polymers or copolymers containing hydrophilic functionality, including polyalkylene glycols (e.g., oligoethylene glycol, polyethylene glycol, polypropylene glycol or polyethylenepropylene glycol, polyethylene oxide, polypropylene oxide), polyvinylpovidone, polyoxazoline, polyzwitterions (such as poly ((3-(methacryloylamino)propyl)-dimethyl(3-sulfopropyl)ammonium hydroxide), poly(2-methacryloxyethylphosphorylcholine), poly polysulfobetaines, polycarbobetaines, etc), polypeptides, polyurethanes, acrylics including 2-hydroxyethylmethacrylate and methoxy- and hydroxy-capped oligoethylene glycol methacrylate, polyacrylamides including carboxybetaine acrylamide, polyesters, polyimide polyether ketone, polyvinyl chloride, or a combination of at least one of the forgoing natural and synthetic polymers. The nonadhesive material can be attached to the substrate in various forms, including adhered to the substrate by physical forces or chemically attached, for example by linkers, and can be water soluble or water-solvated. In an embodiment, the nonadhesive material is a polymer that is sterically repulsive to bacteria and is net charge neutral. The components of the nonadhesive feature, for example the natural or synthetic polymer, can be part of a polymer, crosslinked, grafted, end-grafted, or otherwise functionalized. The chains of the natural or synthetic polymer can be extended, in a random coil, folded, or partially extended. The components of the non-adhesive features, for example the natural or synthetic polymer, oligomer, or amphiphile, if not crosslinked, can have a molecular weight of about 0.15 to 200 kiloDaltons. In an embodiment, a polymer is presented as an end-grafted architecture or polymer brush. Polymer brushes are often characterized by a high density of grafted chains. In another embodiment, the polymer is zwitterionic, for example polymers derived from betaines, phosphorylcholine-substituted methacrylic polymers, or vinyl benzene imidazole polymers.

In a specific embodiment, the synthetic polymer is a polypropylene glycol (a higher molecular weights known as polypropylene oxide, PPO) or polyethylene glycol (at higher molecular weights known as polyethylene oxide, PEO), fix example a polyethylene glycol having the formula

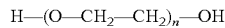

H—(O—CH$_2$—CH$_2$)$_n$—OH wherein n is about 3 to about 10,000. The polyethylene glycol can be grafted, or functionalized to modify a property thereof, and can be present as a polymer brush.

The adhesive element can be a modified portion of the nonadhesive feature, for example the natural or synthetic polymer wherein discrete nanoregions of the polymer may have been modified (e.g., functionalized) to be adhesive to bacteria. Alternatively, the adhesive elements can be discrete molecules or particles associated with the biologically or bacterially nonadhesive feature. Thus, the adhesive elements can be a natural polymer such as a polypeptide or a protein, chitosan, a synthetic polymer or polymer nanoparticle, including a cationic and/or hydrophobic synthetic polymer, a cationic and/or hydrophobic dendrimer; or a cationically functionalized moiety, for example a cationically-functionalized hydrophobic synthetic polymer, a cationically-functionalized hydrophobic synthetic polymer particle, a cationically-functionalized dendrimer, a cationically-functionalized hydrophobic nanoparticle, or a cationically and/or hydrophobically-functionalized inorganic nanoparticle; or combination comprising at least one of the foregoing. The nanoregions or nanoparticles can be of any shape, regular or irregular. The regions or particles can have an average largest dimension of about 3 to about 100 nanometers (nm), specifically about 5 to about 50 nm.

In an embodiment the adhesive element can comprise a natural polymer or a synthetic polymer that is charged, neutral, zwitterionic, hydrophobic, or a combination comprising at least one of the foregoing. Examples of natural polymers include a polypeptide, a protein, chitosan or a combination comprising at least one of the foregoing. Examples of synthetic polymers include various polyamines, polyacrylonitrile, polyacrylic acid, polyacrylate, polymethacrylic acid, polymethacrylate (e.g., polymethyl methacrylate), or a combination comprising at least one of the foregoing.

In an embodiment the adhesive element is a natural polymer, in particular a peptide or a protein, for example a cationic polypeptide or protein containing, for example L-lysine. The L-lysine can be present in amounts sufficient to provide an overall positive charge to the protein or peptide, or the polypeptide can be a homopolypeptide containing, for example, L-lysine. The polypeptide can comprise about 20 to about 500 structural units. The polypeptide such as poly-l-lysine can be in the form of a coil.

In still another embodiment the adhesive element can be a cationically and/or hydrophobically-functionalized inorganic nanoparticle comprising, for example, a metal, a metal oxide, or a ceramic core, for example an amine-functionalized silica nanoparticle such as Ludox. Another example is a cationically and/or hydrophobically-functionalized metal nanoparticle of Groups 10 to 11 of the Periodic Table of the Elements, for example gold. The cationically and/or hydrophobically-functionalized nanoparticle can comprise a gold core having an average diameter of about 2 to about 20 nanometers and having about 30 to about 2000 ligands disposed thereon, for example 1-mercaptoundecane and N,N,N,-trimethyl(11-mercaptoundecyl)ammonium chloride. The functionalized nanoparticle can have a dimension of about 3 to about 20 nanometers.

A combination of any of the foregoing adhesive elements can be used, for example to provide a desired selectivity, or to capture different types of bacteria, or to provide both optimal capture and optimal killing. Regarding selectivity, the surfaces containing the adhesive elements as described above are advantageous compared to prior art methods. For example, antibody-containing surfaces have been used for selective bacterial capture. However the surfaces described above do not rely on anti-body type molecular recognition. As a result of not using antibodies, they are more economical to produce.

In an embodiment, the adhesive elements are more toxic to bacteria when associated with the biologically or bacterially nonadhesive surface than when free in solution. Surfaces containing such adhesive elements can have the additional benefit of low toxicity in the event that the adhesive elements are released from the surface, providing "fail safe" materials.

The adhesive elements can be present on the surface at a spatial density of about 1 element per square micrometer to about 50,000 elements per square micrometer, or about 100 elements per square micrometer to about 2000 elements per square micrometer. Effective spatial density can vary widely depending on variables such as charge, molecular weight, physical dimension of the adhesive elements, positioning of the adhesive elements, ionic strength of the fluid, flow rate of the fluid, and other factors. Results with the four different surface designs as described in the Examples demonstrate that lower overall cationic charge density is associated with slower growth of bacterial adhesion, which is consistent with electrostatic-driven increases in adhesion after bacteria capture. Positioning adhesive functionality in nanoscale clusters can also be important, although the relative importance of overall density of adhesive functionality versus clustering is complex. Clustering can be important to the ability of surfaces with low adhesive functionality to capture bacteria at all (see FIG. 8). More uniform distribution of the same numbers of cationic charges on equivalent surfaces will fail to capture round negative objects compared with clustered cationic charge on a collector. Clustering charge or other adhesive functionality can also provide strong killing action of the surface, combined with ease of bacterial release.

Therefore, with a practical goal of adhering and then releasing bacteria, the clustered presentation of adhesive functionality can be a key design consideration. Low density of functionality can facilitate bacterial release by limiting the ultimate adhesion, while clustering facilitates bacteria capture on these surfaces of extremely low overall adhesive functionality. Charge presentation is an additional consideration.

In the embodiments of the method, the above-described surface is contacted with a fluid containing bacteria under conditions effective to adhere the bacteria. The fluid is generally aqueous, e.g., at least 50 volume % (vol %), at least 80 vol %, at least 90 vol %, or at least 95 vol % of the fluid is water, or 99.5 to 100 vol % of the fluid is water. Effective conditions depend on the particular surface used and the configuration of the adhesive elements, the particular bacterial being captured, and the desired selectivity of the capture. In an embodiment, the ionic strength of the bacterial suspension could be between 0 and 10 M, or more specifically between 0 and 1 M, or more specifically between 0 and 0.2 M. Bacterial capture may occur under quiescent or flow conditions where the flow may be shearing flow or it may be a more complex flow geometry such as an impinging jet, or simply submergence of the surface in a container that is somehow mixed.

After capture, the bacteria can be released (i.e., removed) from the surface by application of gentle physical force, rather than the harsher chemical methods described in the art. For example, simple rinsing under low flow conditions or low shear conditions, or physical contact, for example with a gas bubble under low pressure conditions can be effective to remove the adhered bacteria. This highly advantageous feature allows use of the method in a wide variety of devices where exposure to harsher chemical conditions is disfavored or not possible without adversely affecting the functioning or life of the device. This feature also allows re-use of the surface over multiple capture/release cycles.

As stated above, removal of the bacteria can be by rinsing with a fluid at low flow rates, for example imparting on the order of picoNewton forces to individual bacteria. The low flow and low shear conditions during bacterial removal vary depending on the surface used, the fluid used, the bacteria, the flow (or quiescent) conditions during deposition and other factors. Exemplary low shear conditions include, for example, a wall shear of 1 to 5000 $s^{-1}$, or 10 to 2000 $s^{-1}$. Alternatively, it has been found that contact with a physical removal agent such as a gas bubble can be used. The ionic strength conditions during removal in shear can be between 0 and 10 M, or more specifically between 0 and 1 M or more specifically still between 0.15 and 1 M. The ionic strength conditions during removal with a physical object such as a bubble can be between 0 and 5 M, or 0 and 7 M, or even up to 10 M.

In an embodiment, the adhesive elements are selected to both capture and kill bacteria, with or without subsequent release from the surface. Bacterial kill can be achieved, for example, where a higher density of adhesive elements are used.

In still another embodiment, the targeted bacteria can be selectively captured in the presence of at least one biological component other than the bacteria. Such selective capture can be followed by release, or by killing, or by killing and release of the bacteria as described above. As used herein the term "biological component" broadly encompasses organisms such as viruses, cells including mammalian cells and non-targeted bacteria as well as organic molecules or polymers having a biological origin or activity, including but not limited to an amino acid, polypeptide, protein, nucleic acid, oligonucleotide, polynucleotide, sugar, oligosaccharide, carbohydrate, metabolite, drug, fats and lipids, or a combination comprising at least one of the foregoing biological components. Selective capture can be achieved by adjusting the adhesion threshold of the surfaces to a value between that of the desired adherend and the biological component.

Systems and devices based on the above-described surfaces and methods include biomedical devices such as implants, textiles, which includes fibers, yarns, and woven and non-woven fabrics, purification devices, and sensors.

The invention is further illustrated in the following Examples, which do not limit the claims.

EXAMPLES

Methods and Materials:

Poly-1-lysine (PLL), having a nominal molecular weight of 20,000 Daltons was purchased from Sigma-Aldrich, and was employed directly as a bacteria-adhesive element.

Cationically/hydrophobically-functionalized gold nanoparticles were also employed as adhesive surface elements. These were synthesized as described in Srivastava, S., Samanta, B., Jordan, B. J., Hong, R., Xiao, Q., Tuominen, M. T. and Rotello, V. M., Integrated magnetic bionanocomposites through nanoparticle-mediated assembly of ferritin. *J. Am. Chem. Soc.* 2007, 129 (38), 11776-11780; and Zhang, J., Srivastava, S., Duffadar, R., Davis, J. M., Rotello, V. M. and Santore, M. M., Manipulating microparticles with single surface-immobilized nanoparticles. *Langmuir* 2008, 24 (13), 6404-6408, the contents of which are herein incorporated by reference in their entirety, consisted of 7.5 nm gold cores with approximately 500 ligands per nanoparticle. Approximately 300 of the ligands were 1-mercaptoundecane and approximately 200 were N,N,N-trimethyl(11-mercaptoundecyl)ammonium chloride, providing 200 cationic groups per nanoparticle.

As a point of comparison, each PLL chain nominally contained 120 monomers, the ionization of which was pH-dependent. Near pH 7, about most of these amines are positively charged. Both the individual PLL particle coils and cationically-hydrophobically-functionalized nanoparticles are about 10 nm in diameter, as determined by light scattering or TEM, respectively.

The same PLL was also used, separately, to anchor PEG chains to the surface and to position the sterically-repulsive PEG brush around the preabsorbed PLL coils or the cationically-functionalized nanoparticles. When PLL was used as the anchoring component of the PEG brush, it was first linked to an amine-reactive PEG to form a bottle-brush or graft copolymer, as originally developed by Huang et al., as disclosed in Huang, N. P., Michel, R., Voros, J., Textor, M., Hofer, R., Rossi, A., Elbert, D. L., Hubbell, J. A. and Spencer, N. D., Poly(L-lysine)-g-poly(ethylene glycol) Layers on metal oxide surfaces: Surface-analytical characterization and resistance to serum and fibrinogen adsorption. Langmuir 2001, 17 (2), 489-498, the content of which is incorporated herein by reference in its entirety, and Kenausis et al., Kenausis, G. L., Voros, J., Elbert, D. L., Huang, N. P., Hofer, R., Ruiz-Taylor, L., Textor, M., Hubbell, J. A. and Spencer, N. D., Poly(L-lysine)-g-poly(ethylene glycol) layers on metal oxide surfaces: Attachment mechanism and effects of polymer architecture on resistance to protein adsorption. J. Phys. Chem. B 2000, 104 (14), 3298-3309. It was found that PLL backbone functionalization of 35% by 2000 Dalton PEG to be adequate. The functionalized PEG in the original references was no longer available so a modified procedure was adopted, in which the reaction of the N-hydroxysuccinimidyl ester of methoxypolyethylene glycol (Laysan Bio Inc.) and the PLL was conducted in pH 9.1 carbonate buffer for 6 hours prior to dialysis against pH 7.4 phosphate buffered saline.

Four different types of surfaces were prepared, all on silica substrates, and are illustrated schematically in FIGS. 2A-2D. Microscope slides were acid etched overnight to produce the silica surface, rinsed thoroughly in deionized water, placed in a slit-shear flow chamber, and adsorbing species deposited. Unless otherwise noted, adsorption was conducted from flowing pH 7.4 buffer (0.002 M $KH_2PO_4$ and 0.008 M $Na_2HPO_4$, having an ionic strength of 0.026 M and Debye length of 2 nm). The wall shear rate during deposition of adsorbing species was 22 $s^{-1}$. The first surface was an adsorbed layer of PLL. This was formed by flowing a 5 ppm solution of PLL in buffer over the slide until the surface was saturated, producing an adsorbed PLL layer of about 0.4 mg/$m^2$. Buffer was then re-injected to clear away free PLL. A second densely functionalized surface was based on the cationically-functionalized nanoparticles. Here nanoparticles at a concentration of 5 ppm in DI (deionized) water were flowed over the surface until saturation (at these low ionic strength conditions), at about 1000 AuNP/$\mu m^2$. DI water was subsequently re-injected to remove nanoparticles from the chamber. These particular nanoparticles were deposited from deionized water because they aggregated in buffer.

For quantitative studies, surfaces with relatively sparse random arrangements of adhesive elements were produced by timed flow of solutions (5 ppm PLL in 0.026 M pH 7 buffer or 5 ppm nanoparticles in DI water) over acid-etched silica surfaces, followed by re-introduction of buffer or deionized water, as appropriate, to stop adsorption short of saturation. These procedures were based on quantitative reflectometry experiments that tracked of PLL or cationic nanoparticles adsorption, in-situ. The two particular sparse surface compositions studied were prepared by the same procedure, often running "blind" in the microscope (used for bacterial studies) without using the reflectometer to track coverage in-situ). The success of this approach is ensured by the highly-controlled and reproducible nature of transport-limited PLL and cationically-functionalized nanoparticle adsorption kinetics.

After the adhesive elements were deposited and the free solution cleared of adsorbing elements, a 100 ppm solution of PLL-PEG in pH 7.4 0.026 M phosphate buffer was reintroduced to backfill the PEG brush on the remaining surface. For quantitative studies, this PLL-PEG solution was allowed to flow until the surface was saturated, typically 10 minutes for the two sparse surface compositions. Also the surfaces containing 1000 nanoparticles/$\mu m^2$ required a small amount of backfill, 0.3 mg/$m^2$ in Table 2, but the saturated PLL surface did not adsorb any PLL-PEG copolymer. After exposure to the PLL-PEG surfaces, bulk solution was again replaced by flowing 0.026 M buffer.

After surfaces were created, the bacteria portion of the study continued in the same slit flow chamber, on a custom optical microscope that orients the substrate perpendicular to the floor, avoiding the impact of gravity on bacteria-surface interactions. A 20× objective provided a large field of observation (240 $\mu m \times 180$ $\mu m$,) to accommodate monitoring large numbers of bacteria. Bacteria were deposited on the surfaces, from pH 7.4 buffer (having an ionic strength of 0.026 M and a Debye length of 2 nm) and a suspension concentration near $2 \times 10^6$ cells/ml, with a wall shear rate of 22 $s^{-1}$. The numbers of bacteria on the surface, during deposition, aging, and shear challenge were recorded on video, and later counted in different frames.

The S. aureus themselves, ATCC 25923, were grown in Luria-Bertani (LB), as is standard. Cultures were incubated overnight, shaking at 200 rpm at 37° C., and then harvested after a total of 24 hours during logarithmic growth. Suspensions were centrifuged at 1000×g and cells subsequently re-suspended in buffer. This washing procedure was repeated twice, and the final bacteria concentration, either $5 \times 10^5$/mL for studies of the capture efficiency, or $2 \times 10^6$/mL for rapid deposition prior to removal studies, was then formulated. Bacteria were stored at 4° C. and used within 24 hours.

Four surface designs, shown schematically in FIG. 2A-D, were used. Preparation of such surfaces is disclosed in Gon, S., Bendersky, M., Ross, J. L. and Santore, M. M., Manipulating Protein Adsorption using a Patchy Protein-Resistant Brush. Langmuir 2010, 26 (14), 12147-12154; Gon, S. and Santore, M. M., Single Component and Selective Competitive Protein Adsorption in a Patchy Polymer Brush: Opposition between Steric Repulsions and Electrostatic Attractions, Langmuir 2011, 27 (4), 1487-1493; Gon, S. and Santore, M. M., Sensitivity of Protein Adsorption to Architectural Variations in a Protein-Resistant Polymer Brush containing Engineered Nano-scale Adhesive Sites, Langmuir 2011, 27, 15083-15091; Gon, S. and Santore, M. M., Interaction of Cationic Proteins and Polypeptides with Biocompatible Cationically-Anchored PEG Brushes, Macromolecules 2011, 44, 8161-8168; and Fang, B., Gon, S., Park, M. H., Kumar, K. N., Rotello, V. M., Nusslein, K. and Santore, M. M., Using Flow to Switch the Valency of Bacterial Capture on Engineered Surfaces Containing Immobilized Nanoparticles. Langmuir 2012, 28 (20), 7803-7810; and Fang and Santore, Coll. Surfaces B, 87(1), 109-115, 2011. In the following Examples, low densities of adhesive functionality are balanced against sufficient adhesive driving force to capture bacteria quickly and semi-permanently in modest flow (corresponding to a wall shear rates of, for example, 5-50 $s^{-1}$).

Poly-1-lysine (PLL) patches and about 10 nm cationically-functionalized gold nanoparticles were used. The initial capture rates for S. aureus on these surfaces are well established: They persist for at least 10 minutes and reflect bacteria-collector interactions without interference from bacteria-bacteria interactions on the surface, as is further disclosed in Gon, S., Kumar, K. N., Nusslein, K. and Santore, M. M., How Bacteria Adhere to Brushy PEG Surfaces: Clinging to Flaws and Compressing the Brush. *Macromolecules* 2012, 45 (20), 8373-8381, and Fang, B., Gon, S., Park, M., Kumar, K. N., Rotello, V. M., Nusslein, K. and Santore, M. M., Bacterial adhesion on hybrid cationic nanoparticle-polymer brush surfaces: Ionic strength tunes capture from monovalent to multivalent binding. *Colloid Surf B-Biointerfaces* 2011, 87 (1), 109-115. The presence of thresholds in the loadings of adhesive elements needed for bacterial capture are shown in FIGS. 3A and 3B. The sparse surfaces for adhesive elements were therefore chosen to be 400 functionalized nanoparticles/$\mu m^2$ and 3500 PLL patches/$\mu m^2$, both of which are appropriately greater than their respective thresholds. The properties of these sparse surfaces are summarized in Table 2 and compared with the more densely cationic surfaces of each type, i.e., surfaces containing 1000 functionalized nanoparticles/$\mu m^2$ and a saturated adsorbed layer of PLL (which contains about 12000 PLL chains/$\mu m^2$).

Table 1 shows features of the surfaces containing sparse loadings of adhesive elements, including their modest net negative zeta potentials. These properties provide for attractive interactions which are localized at the positions of the cationic PLL and nanoparticle elements, the remainder of the surface presents a sterically repulsive PEG brush and provides a net negative charge beneath the brush and is repulsive to negative bacteria.

TABLE 1

Properties of Surfaces

| Adhesive Elements | Saturated PLL Coils | Sparse PLL Coils | Saturated Nano-particles | Sparse nano-particles | Plain PEG Brush |
|---|---|---|---|---|---|
| Surface Density, # elements/$\mu m^2$ | 12,000 | 3,500 | 1000 | 400 | 0 |
| Average element spacing, nm | — | 17 | 32 | 50 | — |
| Overall PLL-PEG content, mg/m$^2$ | 0 | 0.61 | 0.3 | 0.67 | 1.1 |
| Zeta Potential, mV* | | | | | |
| $\kappa^{-1} = 1$ nm | 2 ± 5 | −12 ± 2 | −19 ± 5 | −22 ± 3 | −17 |
| $\kappa^{-1} = 2$ nm | 6 ± 2 | −20 ± 3 | −20 ± 4 | −27 ± 3 | −27 |
| $\kappa^{-1} = 4$ nm | 4 ± 2 | −23 ± 4 | −30 ± 3 | −37 ± 3 | −30 |
| Averaged density of positive charge, #/$\mu m^2$ | $1.4 \times 10^6$ | $4.2 \times 10^5$ | $2.0 \times 10^5$ | $8.0 \times 10^4$ | — |

Table 1 shows the estimated average density of positive adhesive charge. This estimate was calculated based on the properties of the elements described in the experimental section and knowledge of their surface loadings. Not all the amine groups can be charged, as they may not all be accessible (for instance the charges beneath the nanoparticles would not be felt by approaching bacteria), and they can be reduced by counterion condensation. Nonetheless, Table 1 presents a first estimate and highlights the greater cationic charge on the PLL patch-containing surfaces compared with the respective nanoparticle-containing surfaces.

Figures 14A, 14B, 14C:
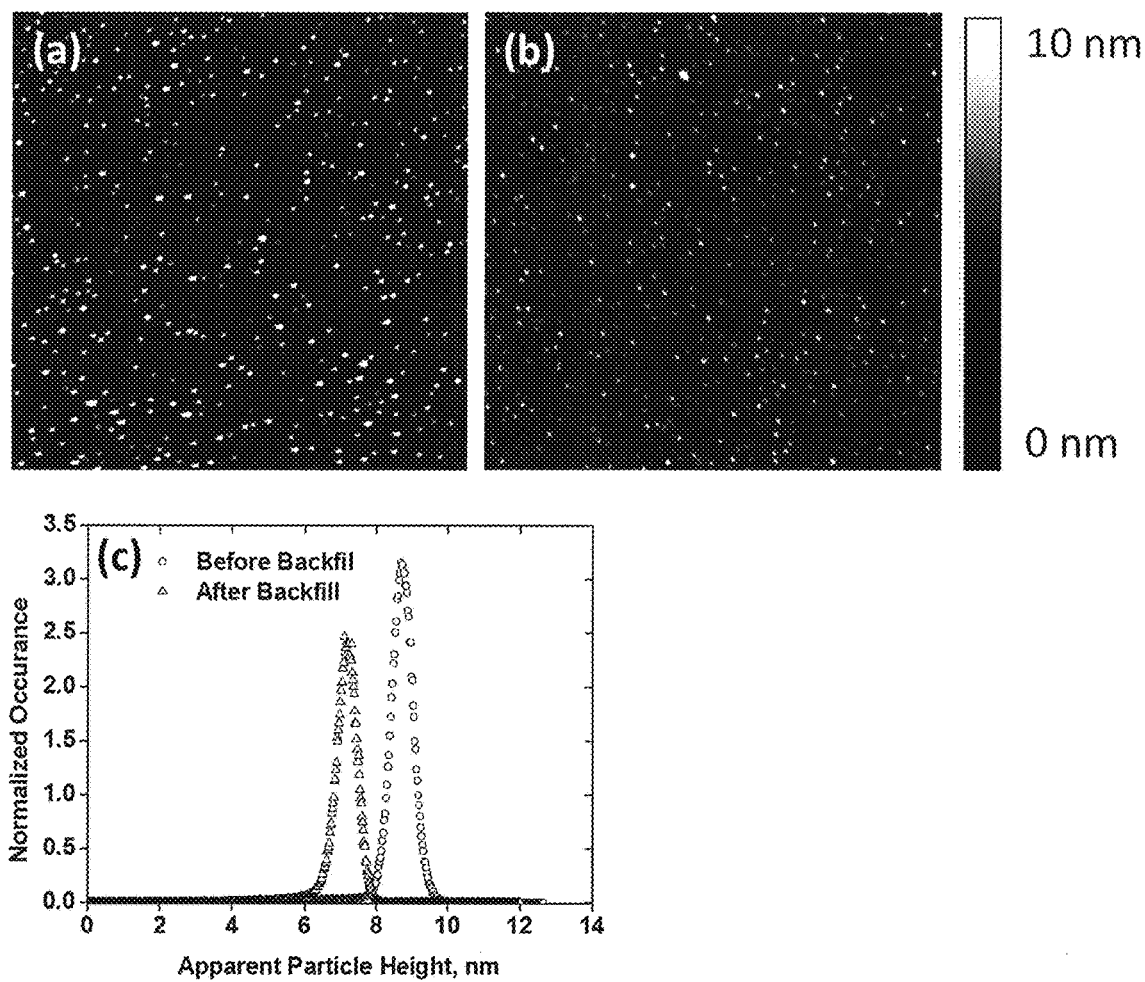
FIGS. 14A-14B show AFM images of two different surfaces having 100 nanoparticles/µm² before (FIG. 14A), and after (FIG. 14B) backfilling with PLL-PEG.
FIG. 14C shows a histogram of apparent particle heights.

FIGS. 14A-14B show AFM images (2×2 μm) of two different nanoparticle-containing surfaces having 100 nanoparticles/$\mu m^2$, (a) before and (b) after backfilling with PLL-PEG. It is noted that particle density is not affected by the backfilling. FIG. 14C shows a histogram of particle heights that the apparent particle height decreases from 8.6 nm to 7.2 nm, upon backfilling.

The micrographs show the random positioning of the nanoparticles and support the previous observation, using Near Brewster reflectometry to probe larger surface areas, that nanoparticles are not removed by the backfilling process. See, B. Fang, S. Gon, M. Park, K. N. Kumar, V. M. Rotello, K. Nusslein, M. M. Santore, Bacterial adhesion on hybrid cationic nanoparticle-polymer brush surfaces: Ionic strength tunes capture from monovalent to multivalent binding, *Colloid Surf B-Biointerfaces* 87, (2011) 109. In FIG. 14, the dry heights of the immobilized nanoparticles slightly exceed 8 nm, as AFM is sensitive to the gold cores and may deform the ligand shells. After backfilling with the PLL-PEG brush and drying, the nanoparticle heights appear about a nanometer shorter because the PLL-PEG is deposited onto the microscope slide and not on the particles. In water, the PEG brushes swell to about 8 nanometers (a calculated estimate). It is noted that solvated brush heights cannot be determined by AFM due to the dilute character of the brush. Thus, during bacteria capture, parts of the nanoparticles are near the brush periphery.

Figures 15A, 15B, 15C:
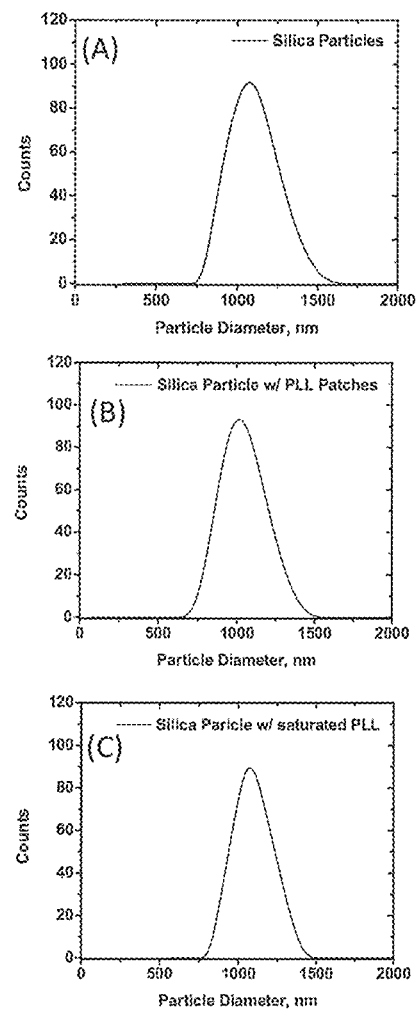
FIGS. 15A-15C are graphs of counts versus particle diameters showing dynamic light scattering from 1 micron silica spheres without added PLL (FIG. 15A), containing 3,500 PLL chains/µm² (FIG. 15B), and saturated with adsorbed PLL (FIG. 15C).

On surfaces containing sparse PLL patches or PLL patches backfilled with a PLL-PEG brush, the PLL patches themselves are quite flat, especially compared with the nanoparticle-containing surfaces. Polyelectrolytes such as PLL, adsorbed on oppositely charged surfaces at moderate ionic strengths, assume flat conformations at the liquid-solid interface, especially at low coverages when adsorbed chains are isolated. This flatness is confirmed by dynamic light scattering as shown in FIG. 15. Data in FIG. 15 show that the hydrodynamic radii of silica particles containing adsorbed PLL are similar to those of bare particles. Additionally, previous single-photon fluorescence microscopy studies established the random arrangement of the PLL chains and their non-aggregated surface state. See, S. Pogodin, J. Hasan, V. A. Baulin, H. K. Webb, V. K. Truong, T. H. P. Nguyen, V. Boshkovikj, C. J. Fluke, G. S. Watson, J. A. Watson, R. J. Crawford, E. P. Ivanova, Biophysical model of bacterial cell interactions with nanopatterned cicada wing surfaces, *Biophys. J.* 104, (2013) 835. From these characterization studies a picture of flat PLL patches embedded within a PLL-PEG brush can be imagined. The in-plane diameter of the adsorbed PLL chains is estimated from the 8 nm coil diameter from dynamic light scattering.

Example 1

Figure 4:
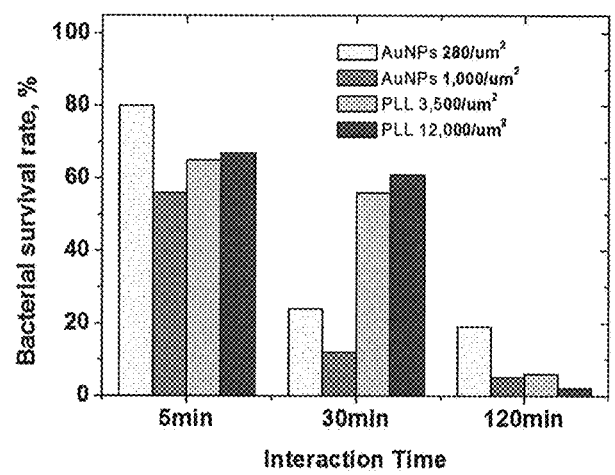
FIG. 4 is a graph of bacterial survival (percent, %) versus interaction time (minutes, min) showing bacterial survival (opposite of killing efficiency) for surfaces with gold nanoparticle (AuNPs) or poly-l-lysine (PLL) coils or "patches" embedded in a 2,000 Dalton polyethylene glycol brush which is, itself, nonadhesive to proteins and bacteria.

This Example illustrates that the disclosed surfaces can have unexpected bacterial killing performance. FIG. 4 shows an example of killing kinetics of *S. aureus* on a series of surfaces having either cationically-functionalized gold nanoparticles (AuNPs) or poly-1-lysine (PLL) patches (single adsorbed polymer coils) embedded in a 2,000 Dalton polyethylene glycol (PEG) brush layer, made as described in Example 5 below. The PEG brush is sufficiently dense in this case, having about 1 mg/m$^2$ of PEG, to provide a strong steric repulsion to objects and molecules in solution. This killing on the surfaces was compared to killing on control surfaces. The graph in FIG. 4 summarizes the results of a standard live-dead staining assay to assess the killing efficiency for bacteria adhering to each surface, from flowing pH 7.4 phosphate buffer with an ionic strength of 0.026 molar (M). For the cationic particle-containing surfaces, the adhesive functionality is clustered in nanoscale particles, as shown schematically in FIGS. 1 and 2. The control surfaces distribute the same adhesive functionality over the entire surface, or the control surfaces are covered with adhesive functionality to the maximum extent possible. The two cationic particle-decorated surfaces having discrete functionality are based on either gold nanoparticles or poly-l-lysine polymer coils, embedded in the sterically repulsive PEG brush layer.

In FIG. 4, a first series of surfaces contain discrete cationic particles (i.e., cationically/hydrophobically-functionalized gold nanoparticles) having an average diameter of about 10 nm (nominal size). In FIG. 4 the second type of discrete adhesive elements are isolated 20 kiloDalton poly-l-lysine (PLL) chains. When adsorbed these particular molecules form locally cationic regions on the surface, or PLL "patches". Both nanoparticles and patches are randomly arranged on their respective glass substrates though the relatively random arrangement and the choice of glass as a model substrate is not limiting. The lack of a constraint for precise positioning of surface elements, for instance, approximate random positioning makes fabrication of these surfaces easy. The cationic nanoparticles protrude forward of the substrate about 8 nm as a result of the deformation of their ligands, while PLL chains adsorb as a flat, e.g., no more than about 2 nm high, random coils, roughly 10 nm in diameter. The portions of the surface not occupied because of the low surface loadings of these adhesive cationic nanoscale elements contain a water-solvated PEG brush, with each PEG tether having a weight of about 2,000 Daltons as described above.

As shown in FIG. 4, S. aureus bacteria that adhere to the Example surfaces are killed relatively rapidly, even with relatively sparse adhesive elements present on the surface. Separate controls confirmed that without the adhesive particles or patches, the surfaces neither capture bacteria nor kill them. Without being bound by theory, in this particular example, the minimum density of adhesive elements to capture the bacteria in gentle flow (about 22 s$^{-1}$ wall shear rate) appears to be about 150 nanoparticles per square micrometer (np/µm$^2$) or about 2500 PLL adhesive elements/µm2, and the killing tests are conducted at densities of adhesive elements just about these thresholds. These threshold surface densities of adhesive elements are reported for an ionic strength of 0.026 M, and the surface density of adhesive element suitable for bacterial capture depends on ionic strength.

There is only a slightly greater killing efficiency, borne out at longer times, when the surfaces are more density functionalized with the same elements, also in FIG. 3. Thus, and while not wanting to be bound by theory, it is understood that bacteria are being killed on surfaces containing as few as 7×10$^{12}$ available cationic charges per cm$^2$ under these experimental conditions. This is more than an order of magnitude lower than the thresholds previously reported. While not wanting to be bound by theory, is understood that the unexpected effectiveness of combined capture and killing is due to the discrete adhesive functionality, in contrast to previous studies that employed uniformly functionalized surfaces.

Example 2

Figure 5A:
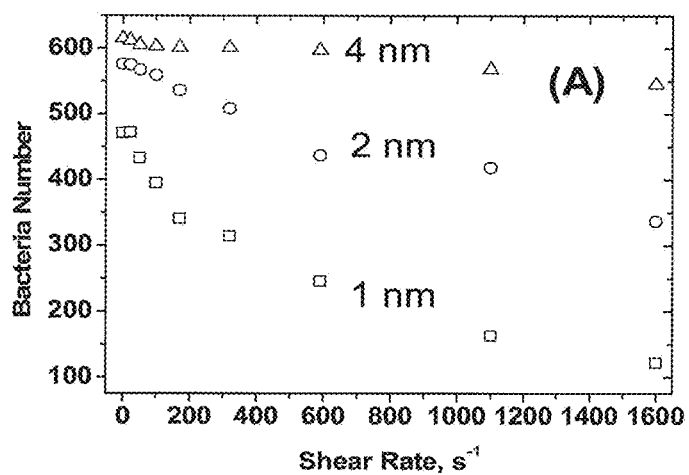
FIGS. 5A and 5B are each graphs of bacteria number versus shear rate (per second, s$^{-1}$), showing the number of bacteria retained after flowing pH 7.4 phosphate buffers having the Debye lengths shown. Experiments are done progressively with increasing shear so that by the time the wall shear rate is 1600 s$^{-1}$, the remaining bacteria have resided on the surface for at least 20 minutes.
Figure 5B:
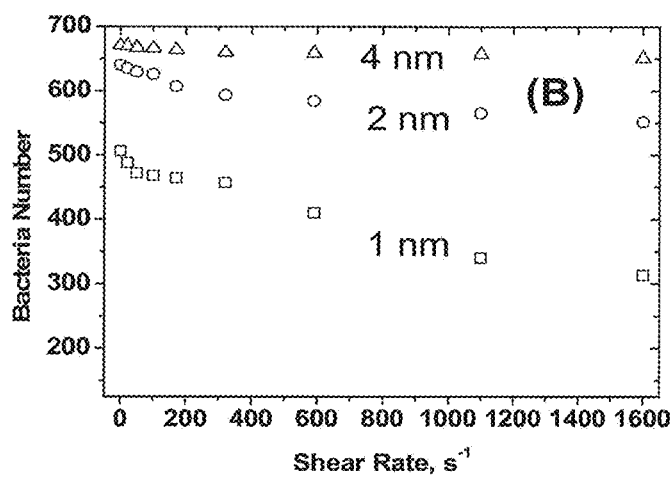

This Example illustrates release of captured bacteria, as well as re-use of the surfaces in multiple capture/release cycles. FIGS. 5A and 5B show data that compares surfaces containing the same adhesive nanoparticle and PLL particles embedded in a 2 kiloDalton PEG brush as in Example 1, with slightly greater densities of nanoparticles: 400 nanoparticles/µm$^2$ in FIG. 5A compared with 280 nanoparticles/µm$^2$ in FIG. 4. This is because 280 nanoparticles/µm$^2$, while deadly in FIG. 4, was so close to the adhesion threshold that it was difficult to get good statistics in bacterial rinsing, though the statistics in bacterial killing (FIG. 4) were very clear. There is more efficient bacterial capture with 400 nanoparticles/µm$^2$ than with 280 nanoparticles/µm$^2$. Thus the rinsing studies of FIG. 5A are done on essentially the same or more densely-functionalized more adhesive surfaces compared with those employed for FIG. 4. Killing studies and removal studies require separate runs because the viability assay interferes with measurements of removal.

It was surprisingly found in these studies that all bacteria were substantially removed in progressively increasing shear, all in the gentle range up to 1600 s$^{-1}$, from the two surfaces when an air bubble was passed over the surface. Air bubbles produce normal forces, compared with shearing forces when the bacteria are completely submerged. The air bubble method is effective to even remove bacterial that have been on the surface for 20 minutes or more. It was further noted that when the surfaces were loaded with the maximum density of adhesive particles, e.g., 1000 nanoparticles/µm$^2$ or 12000 PLL patches per µm$^2$, it was very difficult to remove the bacteria using shear forces. The use of sparsely loaded (e.g., about 300 #/µm$^2$) nanoscale adhesive elements produces a surface which kills most bacteria within 30 minutes and from which bacteria can be cleared without aggressive treatment.

Figure 6A:
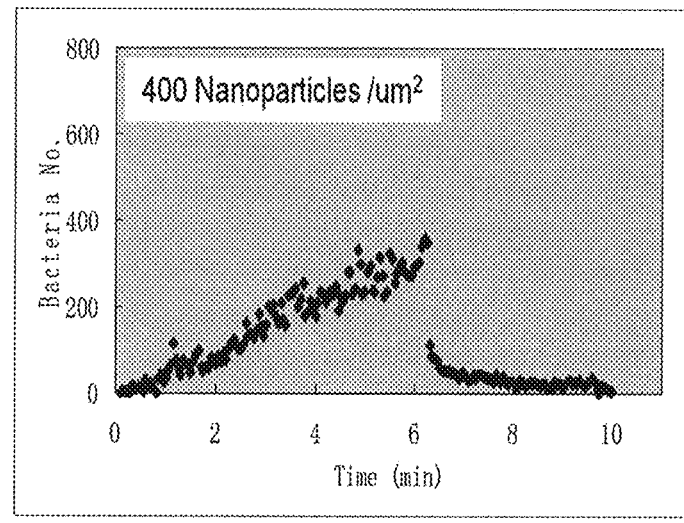
FIGS. 6A and 6B are graphs of bacteria number versus time (minutes, min) which show that adherent S. aureus, captured from flow at a wall shear of 22 s$^{-1}$ and incubated for 6 minutes, are completely removed when the wall shear rate increases to 1600 s$^{-1}$ pH 7.4, wherein ionic strength I=0.026 M. Parts A and B of the figure are for different surfaces.
Figure 6B:
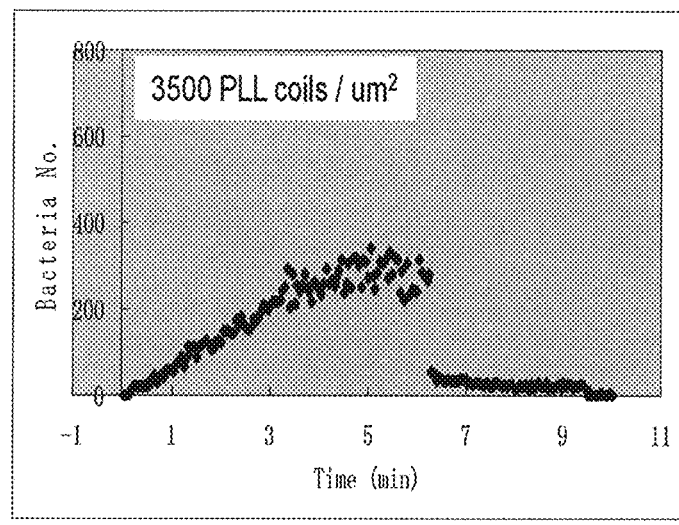

FIGS. 6A and 6B show that on the same sparsely functionalized surfaces, bacteria that have been captured from gentle flow are completely removed from the surface when the flow rate is increased to 1600 s$^{-1}$ 6 minutes after initial capture. Data described in more detail below (FIG. 10D, e.g.) show that complete bacterial removal can be achieved after longer residence times, for example 30 minutes or longer.

Figure 7A:
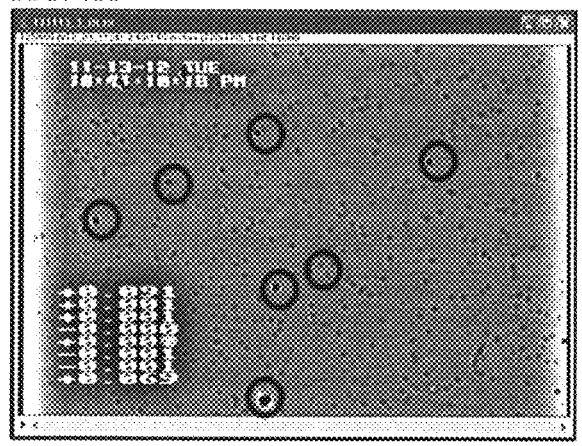
FIG. 7A is an image of bacteria adhesion on a surface containing 400 nanoparticles/μm$^2$.
Figure 7B:
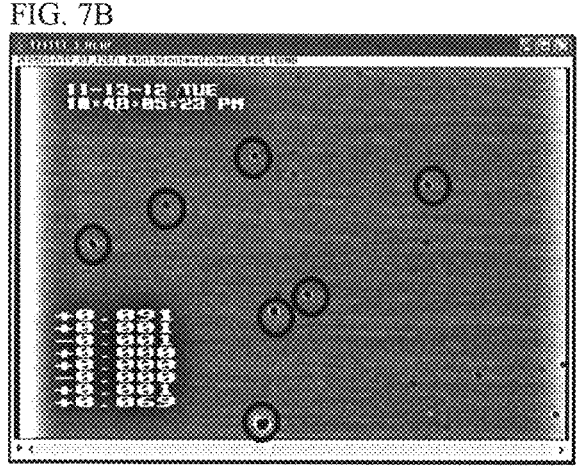
FIG. 7B is the surface of 7A surface after bacterial clearance by an air bubble.
Figure 7C:
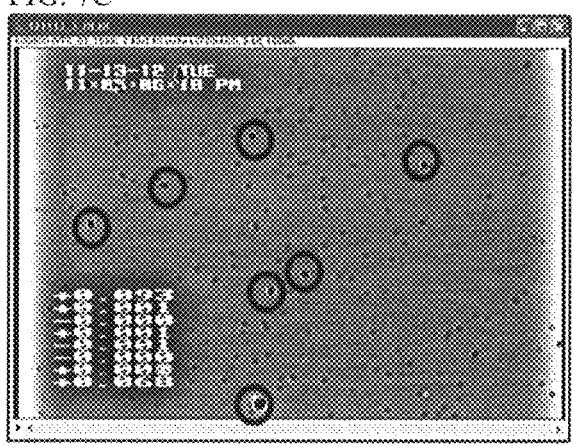
FIG. 7C is the surface of 7B after second exposure to bacteria, wherein in FIGS. 7A-7C, features circled are artifacts on the CCD camera.

FIGS. 7A-C show three images of the same surface containing 400 nanoparticles/µm$^2$ (too small to be visible), in a 2 kiloDalton PEG brush. Such brushes are described in Fang and Santore, Coll. Surfaces B, 87(1), 109-115, 2011. In FIG. 7A, bacteria initially captured on the surface are shown. The surface cleared completely when an air bubble was passed over it in FIG. 7B, and then, in FIG. 7C, new bacteria are captured on a second exposure.

Figures 16A, 16B, 16C, 16D, 16E, 16F:
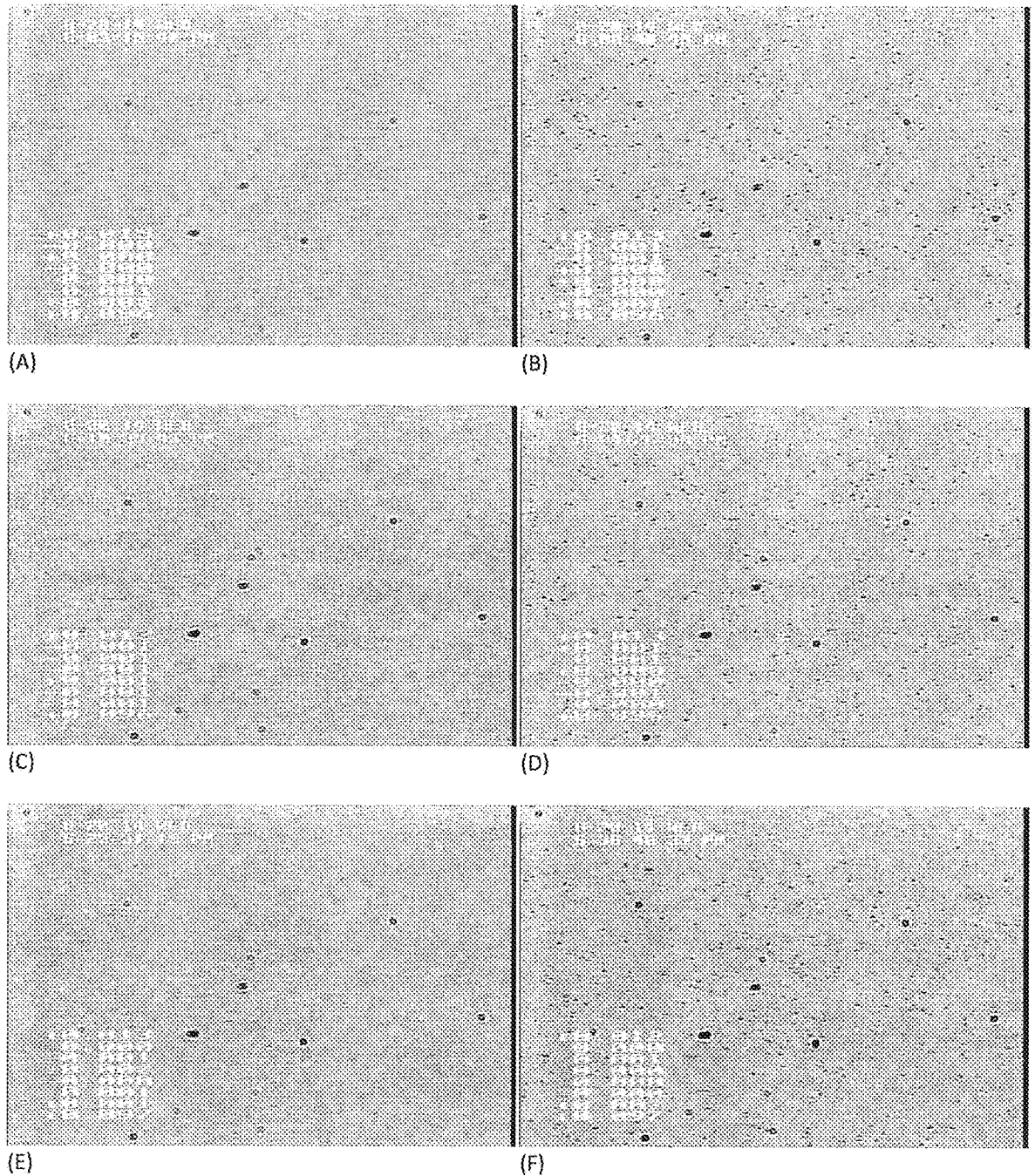
FIGS. 16A-16H show four sets (eight) of images of same surface containing 600 nanoparticles/µm².
Figures 16G, 16H:
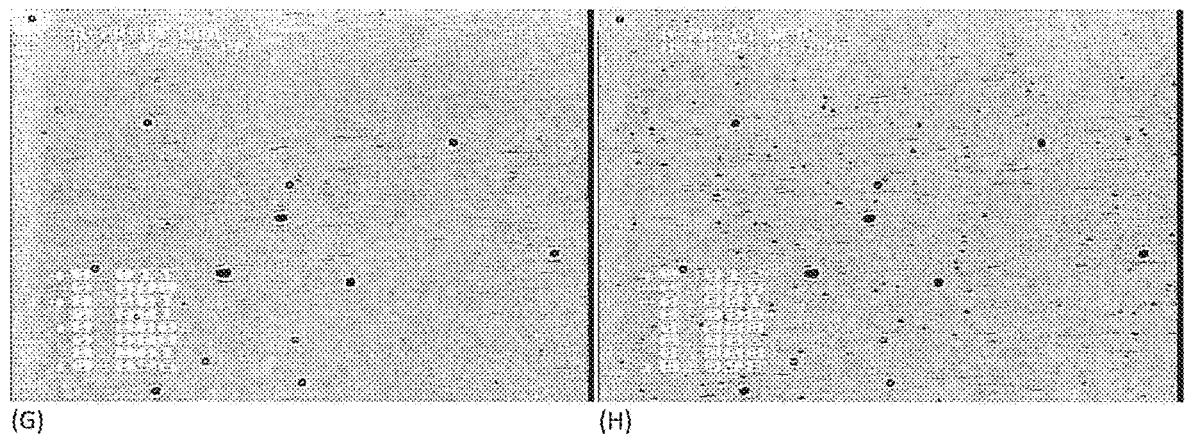
Figure 17:
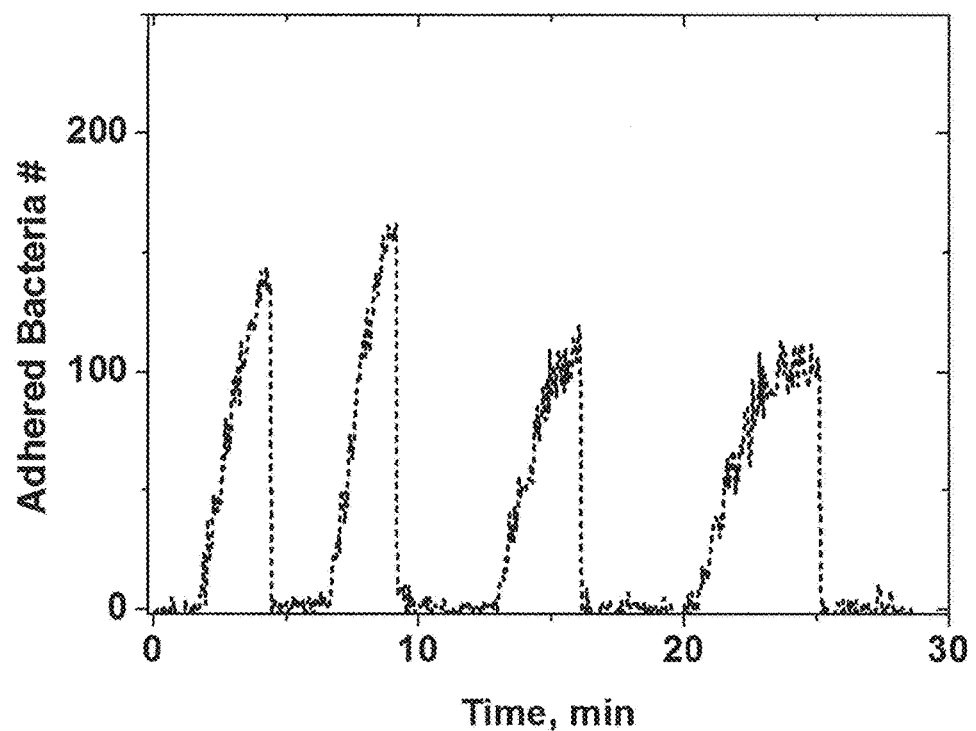
FIG. 17 shows adhesion kinetics of the bacterial cells during multiple exposures and bubble injection (bacteria release) runs on the surface containing 600 nanoparticles/ recorded by a lateral microscope and analyzed by Image-J.
Figure 18:
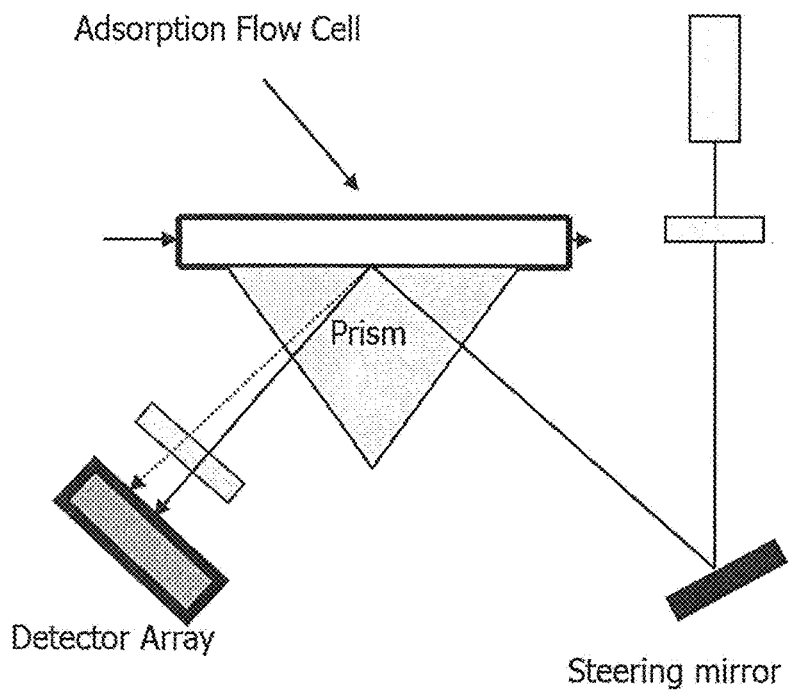
FIG. 18 is a schematic diagram of equipment set-up used for determination of protein/cell adhesion by near-brewster angle reflectometry.
Figure 19:
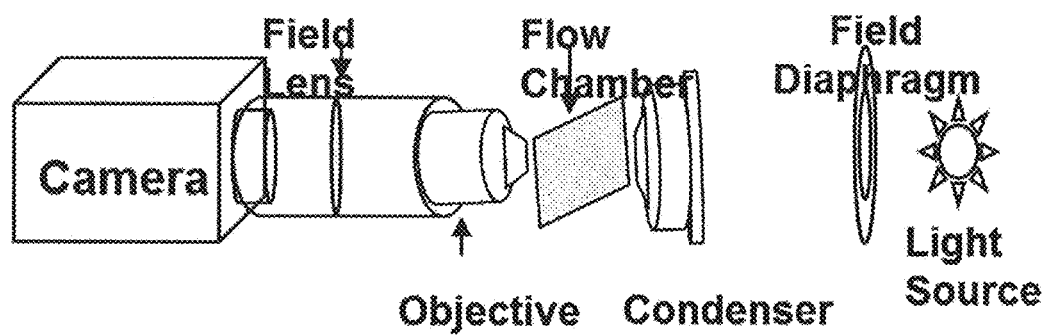
FIG. 19 is a schematic diagram of equipment set-up used for determination of cell adhesion by lateral microscope.
Figure 20:
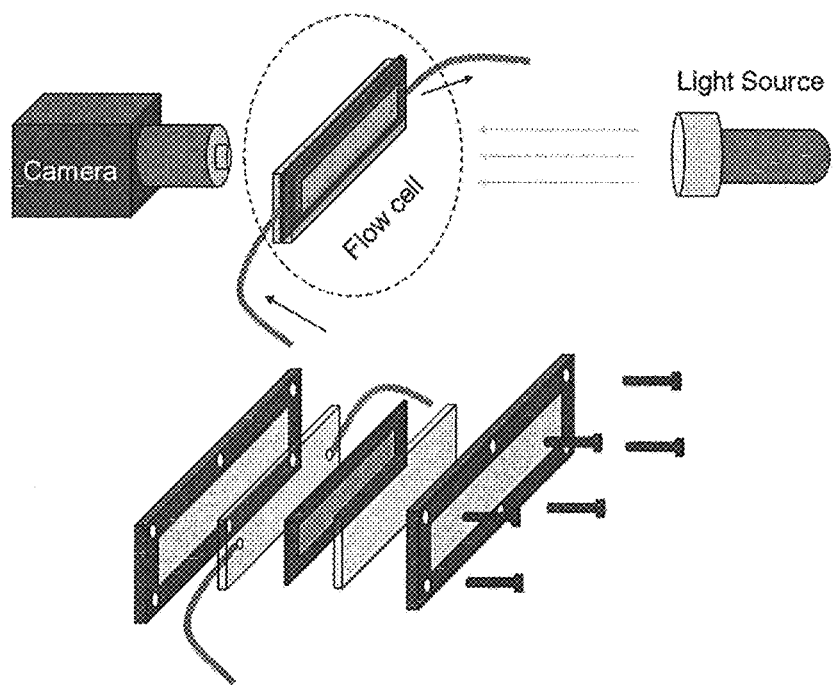
FIG. 20 is a schematic diagram of flow cell set-up for lateral microscope measurements.
Figure 21:
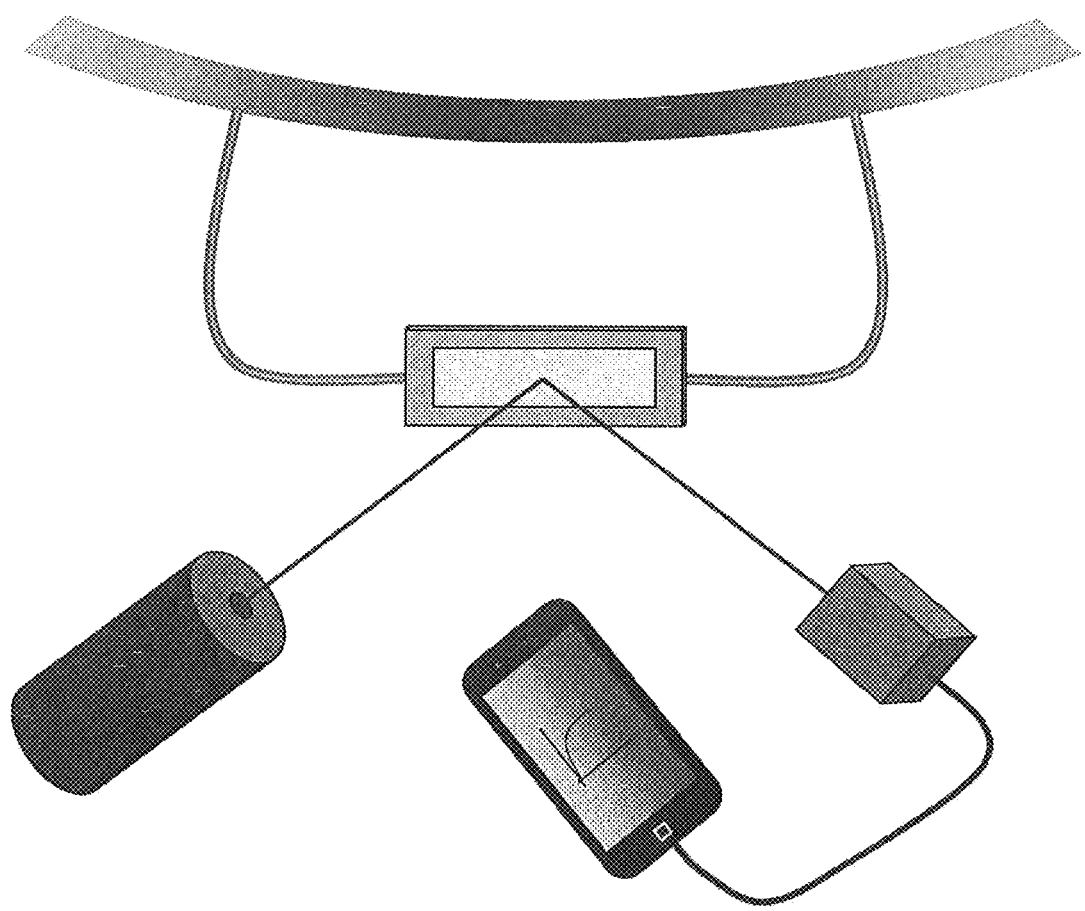
FIG. 21 is a schematic diagram of an alternative set-up of the flow cell.

FIGS. 16A-H show eight images of same surface containing 600 nanoparticles/µm$^2$, in a 2 kiloDalton PEG brush. FIGS. 16A and 16B relate to a first run of bacterial capture and release. FIGS. 16C and 16D relate to a second run of bacterial capture and release. FIGS. 16E and 16F relate to a third run of bacterial capture and release. FIGS. 16G and 16H relate to a fourth run of bacterial capture and release. In these runs, the bacterial cells were suspended in a phosphate buffer (pH=7.4, I=0.026 M) at a concentration of 2×10$^6$/ml. The adhesion shear rate was 225$^{-1}$, while cleaning was done by air-bubble blowing. FIGS. 16A-16H illustrates that the surface cleared completely when air bubble was passed over it and then re-captured bacteria for a total of four exposures. FIG. 17 shows adhesion kinetics of the bacterial cells on the surface during multiple exposures and bubble injections runs.

Example 3

This example illustrates that surfaces can be engineered with selectivity towards different bacterial strains or proteins. S. aureus and proteins found in blood do not adhere to properly designed and synthesized surfaces having 2 kiloDalton PEG brushes. When increasing amounts of adhesive cationic elements, e.g., functionalized gold nanoparticles or PLL patches, are disposed on the surface within the PEG brush, the surfaces remain nonadhesive to proteins and bacteria until a threshold density of adhesive elements is reached. FIG. 3 illustrates this effect, called an adhesion threshold.

Figure 8:
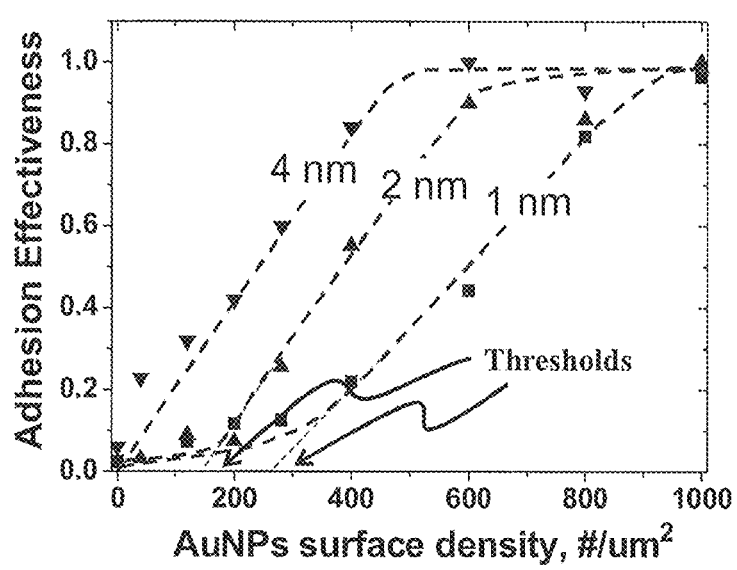
FIG. 8 is a graph of adhesion efficiency versus cationically-functionalized gold nanoparticle surface density (particles per square micrometer, #/μm$^2$) showing adhesion thresholds for S. aureus capture from flow at 22 s$^{-1}$, pH 7.4 and various ionic strengths on surfaces with different nanoparticle loadings into a polyethylene glycol brush. (The labels of 1, 2, and 4 nm indicate the Debye lengths at these ionic strengths).

The surfaces in FIG. 8 are the larger family from which the 280 and 400 adhesive elements/µm² surfaces of FIGS. 4-7 were taken. Because the cationic/hydrophobic nanoparticles have weak binding per adhesive element, multiple adhesive elements engage to capture each bacterium. The effect is sensitive to both the element-bacteria-surface interaction and to physical features of the bacterium. Therefore, different bacteria, with different surface physical chemistries and other surface features, and having different sizes and shapes will tend to exhibit different adhesion thresholds. Surfaces that can distinguish between different bacteria will have an adhesion threshold between the adhesion thresholds of competing species. In another embodiment, it is possible to capture bacteria in the presence of proteins by adjusting the adhesion of the surface to be between the adhesion thresholds of the bacteria and the protein. Of course, the surfaces can only selectively adhere bacteria from protein solutions, without being fouled by proteins, as long as the proteins do not directly adhere to the surfaces of the bacteria.

Example 4

This Example illustrates that when certain adhesive elements, for example cationic/hydrophobic nanoparticles, are immobilized on the surface as in FIGS. 1 and 2, the resulting surfaces can be more lethal to bacteria than the free nanoparticles in solution. While classical optical density methods for determining the minimum inhibitory concentration (MIC) fail due to flocculation of bacteria by nanoparticles, a careful standardized colony-forming unit assay in suspension reveals that the MIC exceeds 500 ppm for the nanoparticles used in FIGS. 4-8. Even using the conservative estimate of 100 ppm nanoparticles in free solution as the benchmark, the data in Table 2 show that the surfaces including the PEG brush layer and the immobilized cationic particles are more efficient at killing bacteria than the same nanoparticles in suspension.

TABLE 2

Nanoparticles in Solution versus on a brushy PEG (2000 MW) Surface

| | Nanoparticle Concentration | Bacteria Concentration | Killing Efficiency |
|---|---|---|---|
| In Solution | 100 ppm = 13.2 nM | $10^5$/mL | 1 (reference) |
| Sparse Surface | 280 nanoparticles/µm² | 500 cells/42000 µm² | 6800 |
| Dense Surface | 1000 nanoparticles/µm² | 800 cells/42000 µm² | 3000 |

Figure 11:
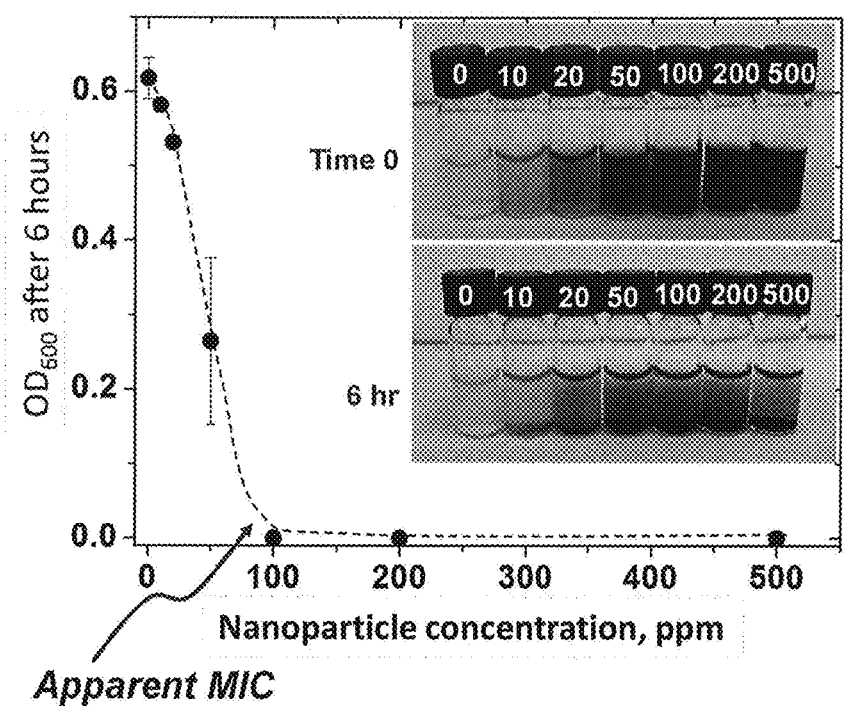
FIG. 11 is a graph of optical density at 600 nm versus nanoparticle concentration in ppm showing results of the classical optical density assay to determine the solution-phase MIC of the nanoparticles. The upper row of photographs shows vials which were photographed immediately after mixing: the contents were 10$^5$/ml S. aureus and the nanoparticle concentrations indicated on the lids (in ppm). The lower row shows photographs of vials after 6 hours at 37° C.

To assess the killing efficiency of free nanoparticles, a classical optical density assay for determination of the minimum inhibitory concentration (MIC) of nanoparticles is carried out. The results are shown in FIG. 11. In this assay, varied amounts of nanoparticles were added to a MH broth containing $10^5$/ml S. aureus (having an optical density, without nanoparticles of OD600=0.001). The optical density of the suspension, after 6 hours of incubation at 37° C. (to allow bacteria to propagate), is classically taken as an indicator of the MIC. A high optical density indicates that bacteria have multiplied in the 6 hour growth period, and a low optical density indicates bacteriocidal activity, or at least inhibition of growth. Following this approach, FIG. 11 suggests an apparent MIC of 100 ppm for the cationic nanoparticles against S. aureus.

While the optical density method is well-accepted for molecular antimicrobials, it is inconclusive for nanoparticle suspensions such as in the present case for the following two reasons. First, adsorption of the nanoparticles on the bacteria causes their aggregation, with bacteria-nanoparticle sediments evident in the inset of the FIG. 11. These sediments deplete bacteria from the main suspension, reducing optical density as an artifact. However, even when bacteria were re-suspended by mixing or by up to 60 minutes of sonication (which were tested to ensure that it did not affect bacterial viability) the optical density of the suspension after 6 hours was always much lower than its initial level. A second problem with the optical density method stems from the standard procedure of using reference solutions comprised of antimicrobial compound (in this case nanoparticles) at each concentration of interest. It was difficult to assess suspended bacteria concentrations because nanoparticle concentrations exceeding ~50 ppm were strongly absorbing at 600 nm, dominating signal from bacteria.

Further, FIG. 11 provides insight into bacteria-nanoparticle interactions in suspension: the images clearly demonstrate the flocculation of the bacteria by adhesion to the nanoparticles. This is significant because, with 95% of the nanoparticles located in bacterial aggregate sediment (an estimate which stems from a visual comparison of supernatant color after 6 hours to that of the initial solutions), it can be certainly determined that the nanoparticles adhered to the bacterial surfaces. The removal of bacteria from the suspension in the presence of nanoparticles was also confirmed by light microscopic observation. Nanoparticles in the absence of bacteria did not settle. Further, we assert that this adhesion/adsorption process occurred in the presence of growth medium, demonstrating that the medium did not interfere with the nanoparticle adhesion to bacteria.

Figure 12:
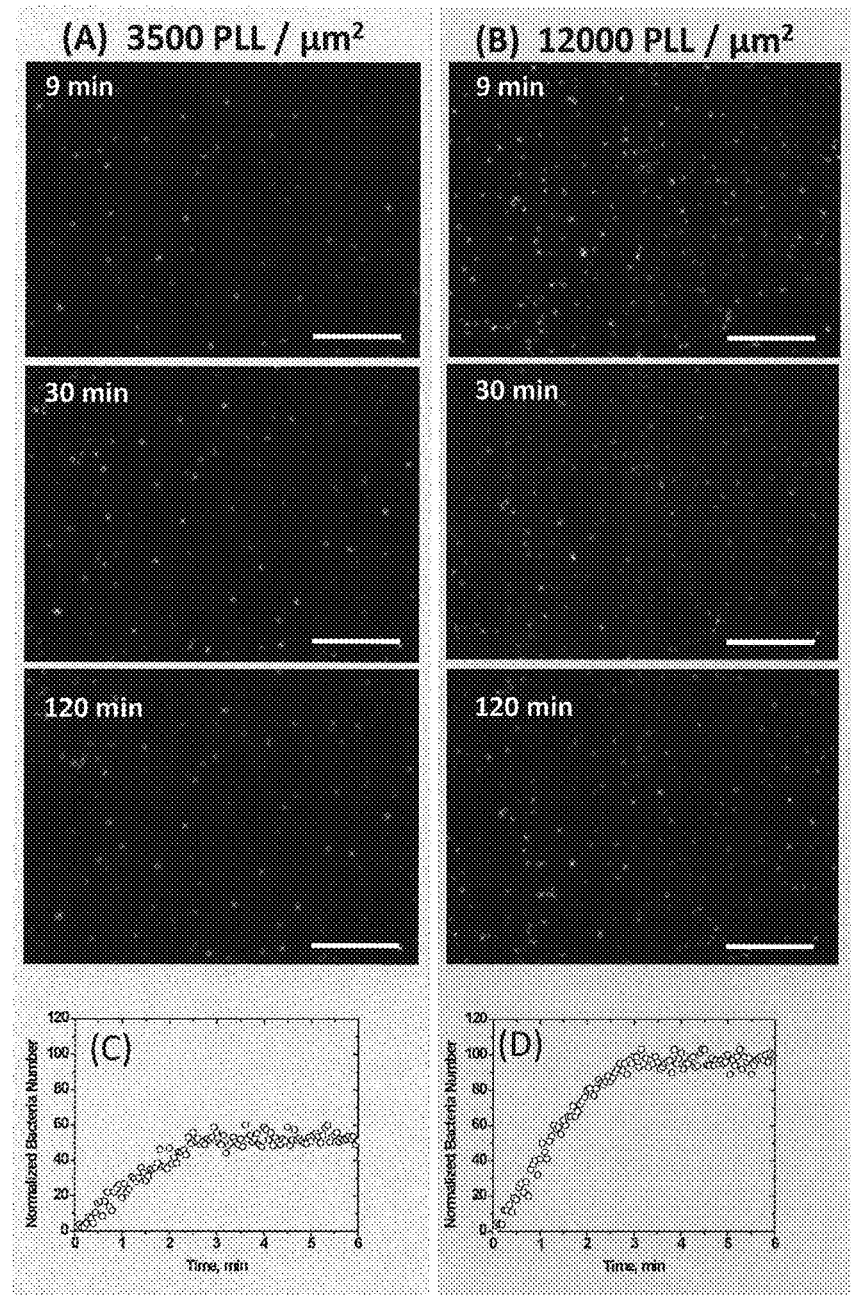
FIGS. 12A-12B show viability of bacterial cells after different exposure times (9 min, 30 min, and 120 min) to the surfaces containing 3,500 PLL coils/μm$^2$ (FIG. 12A) and 12,000 PLL coils/μm$^2$ (FIG. 12B). The red color dots indicates dead bacteria, while green color dots indicate living bacteria.
FIGS. 12C-12D are graphs of normalized bacterial number versus time showing bacterial capture kinetics on the 3,500 PLL coils/μm$^2$ (FIG. 12C) and 12,000 PLL coils/μm$^2$ (FIG. 12D).

These complexities necessitated other methods to assess nanoparticle killing activity in solution. Using a standard CFU (colony forming unit) assay, the viability of S. aureus ($10^5$/ml), incubated at 37° C. for 6 h in MH broth with 500 ppm nanoparticles was assessed. FIG. 12 illustrates that agar plates inoculated with a nanoparticle-bacteria suspension, diluted to $10^3$ cells/ml (based on the original microscopic count), show substantial colony growth and, with live dead staining, nearly no killing. The colony numbers and viability are similar to a bacterial suspension of the same concentration without nanoparticles. These results, combined with the observations in FIG. 11, argue that in the presence of MH broth, S. aureus are not substantially killed by up to 500 ppm nanoparticles though the nanoparticles do, for the most part, adhere to the bacterial surfaces. Even with the established association of substantial numbers of nanoparticles with S. aureus in the sediment, it is considered a possibility that interaction of the growth medium with the bacteria or the nanoparticles inhibited the nanoparticle's killing action. Another possibility is that bacteria are more readily killed in buffer than they are in MH broth. To address both possibilities, the solution-phase killing action of 500 ppm nanoparticles on S. aureus bacteria in phosphate buffer was studied. It is summarized in FIG. 13. The overall nanoparticle concentration was fixed at 500 ppm, and the bacteria concentration was varied from $10^5$ to $10^8$/ml to vary the nanoparticle/bacteria ratio. Nanoparticle-bacteria aggregation was apparent shortly after mixing. By 4 hours, nearly complete settling of bacteria had occurred. In the cases with the greatest bacteria concentrations, this completely removed the nanoparticles from the supernatant, indicating adhesion of all nanoparticles onto the bacteria. With fewer bacteria dosed with the nanoparticles, however, the presence of excess nanoparticles suspended in solution suggested that the settled bacteria were already saturated with nanoparticles. The panels of the figure list the estimated numbers of nanoparticles per original bacterium.

The viability of the suspension-phase (or aggregated) bacteria was studied by live dead staining as shown in FIG. 13. Nearly all bacteria are living, despite exposure to and contact with large numbers of nanoparticles. Large numbers of viable bacteria were additionally confirmed by CFU (not shown). It is noted with $10^5$ bacteria/ml that the bacteria were too sparse to be reliably visualized with live dead staining. Nonetheless, the CFU method revealed substantial bacteria viability.

Example 5

Figure 9A:
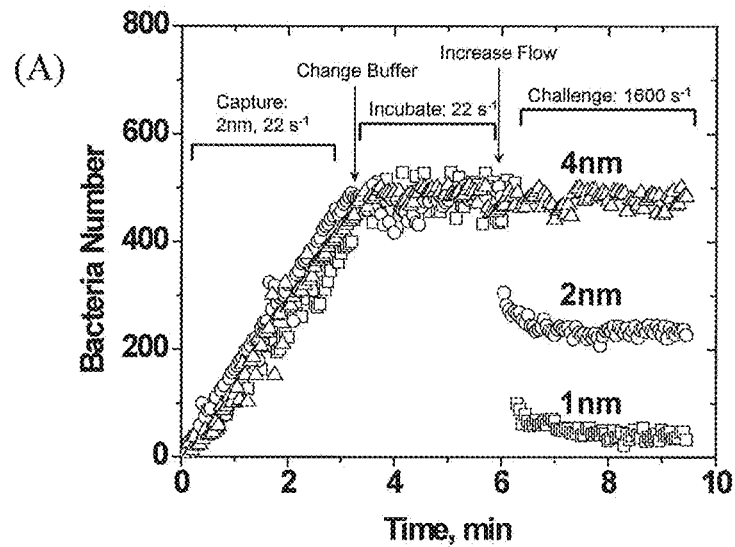
FIG. 9A is a graph of bacteria number versus time (minutes) showing the results of bacterial capture, aging, and shear challenge on surfaces containing 3500 poly-l-lysine patches/μm$^2$.

This Example illustrates bacterial removal at shear exceeding that occurring during bacterial capture. Bacteria were deposited from gently flowing buffer (at a wall shear rate of 22 s$^{-1}$, having an ionic strength of 0.026 M and a Debye length of $\kappa^{-1}$=2 nm), incubated at the ionic strength of choice for a controlled period of time, and then challenged at the elevated wall shear rate, 1600 s$^{-1}$. FIG. 9 shows an example for three sparse PLL surfaces. The runs include a 3-minute bacteria deposition period, (capturing several hundred bacteria in the field of view), introduction of the test buffer, aging for the desired time, and then the increase in flow to a wall shear rate of 1600 s$^{-1}$. In the case of the nominal "5 minute" surface residence period shown in FIG. 9A, the bacteria were aged in test buffer for 3 minutes prior to the high shear challenge, to give an average surface residence time (including a portion of the deposition process) near 5 minutes. For longer nominal aging periods of 15 and 30 minutes in other runs, the aging time was substantially longer than the deposition period so that the nominal times represented the aging times to within 10%.

FIG. 9A illustrates features of bacterial removal from a surface with a PEG brush and PLL adhesive elements. First, the removal rates are fast once the shear is increased. Bacteria sufficiently weakly bound to be removed at elevated shear rates leave the surface almost immediately, while the rest are retained. No long term bacterial loss in extended flow, up to half an hour wall shear rates of 1600 s$^{-1}$ was observed. The rapid bacterial removal rates upon increase in shear, seen in FIG. 9, were characteristic of all surfaces when removal did occur, independent of ionic strength. For the bacterial populations that were removed, a quantitative assessment of the disbonding rate was not possible because the process was so rapid. Because bacteria that are removed at a wall shear rate of 1600 s$^{-1}$ come off so quickly while the retained population is stable, therefore the size of the retained population (relative to the original) is meaningful.

Figure 9B:
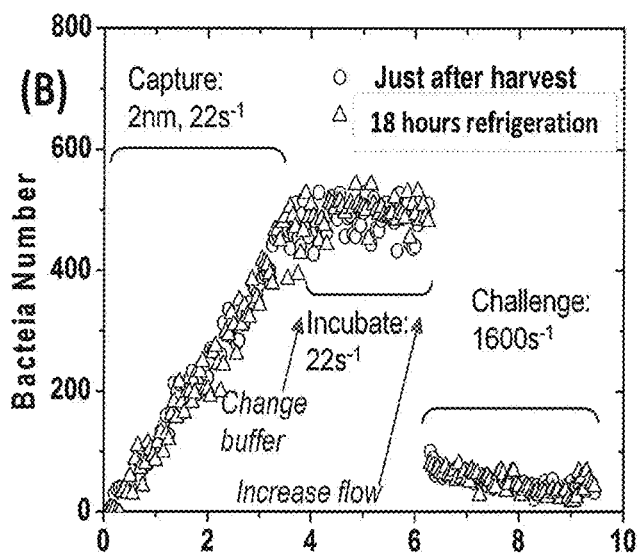
FIGS. 9B to 9D are graphs of bacteria number versus time (minutes) showing the results of bacterial capture, aging, and shear challenge for fresh bacteria compared to those refrigerated 19 hours prior to study.
Figures 9C, 9D:
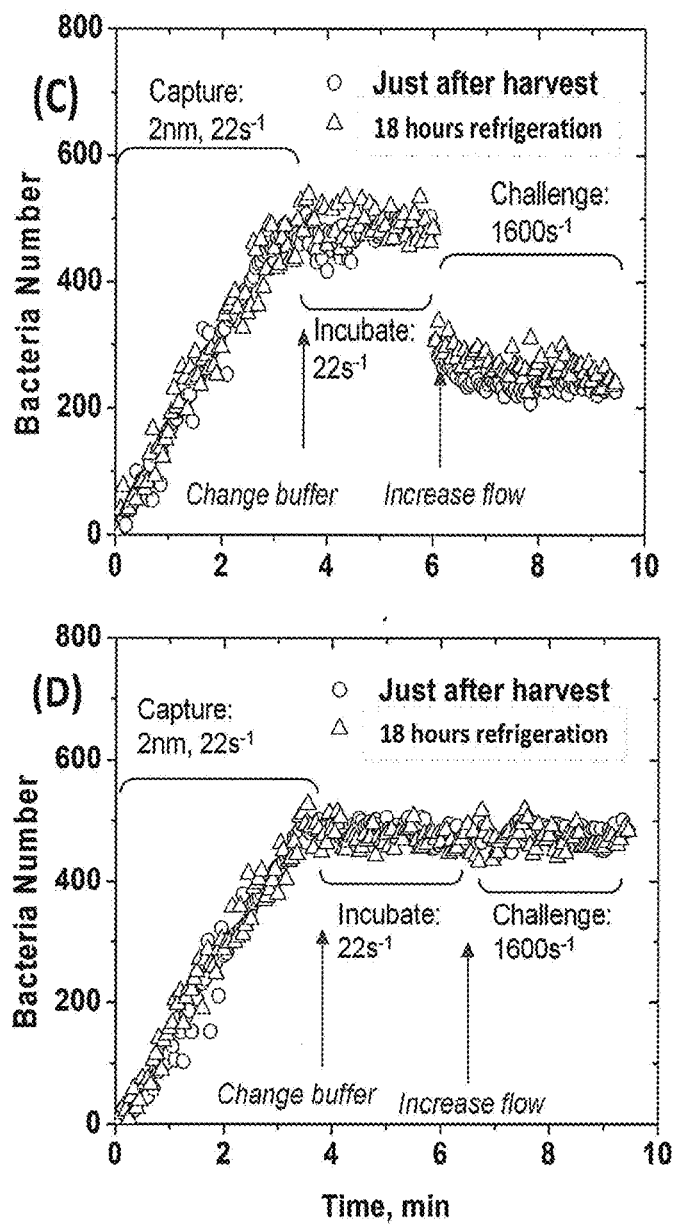

FIGS. 9B-9D show example runs, comparing the behavior of fresh bacteria used in a particular adhesion run to a repeat run for the same conditions (i.e. choice of surface, ionic strength, surface residence time), but with older bacteria (the last run for a particular bacterial batch). FIGS. 9B-9D demonstrates that the test runs with two different ages of bacteria, within the range studied, are nearly indistinguishable. For the three examples shown, which are the runs with the greatest sensitivity to ionic strength, where there is the greatest need for precision in distinguishing the retained and removed populations. This reproducibility is typical of all the runs and test conditions examined by the inventors.

Figures 10A, 10B, 10C, 10D:
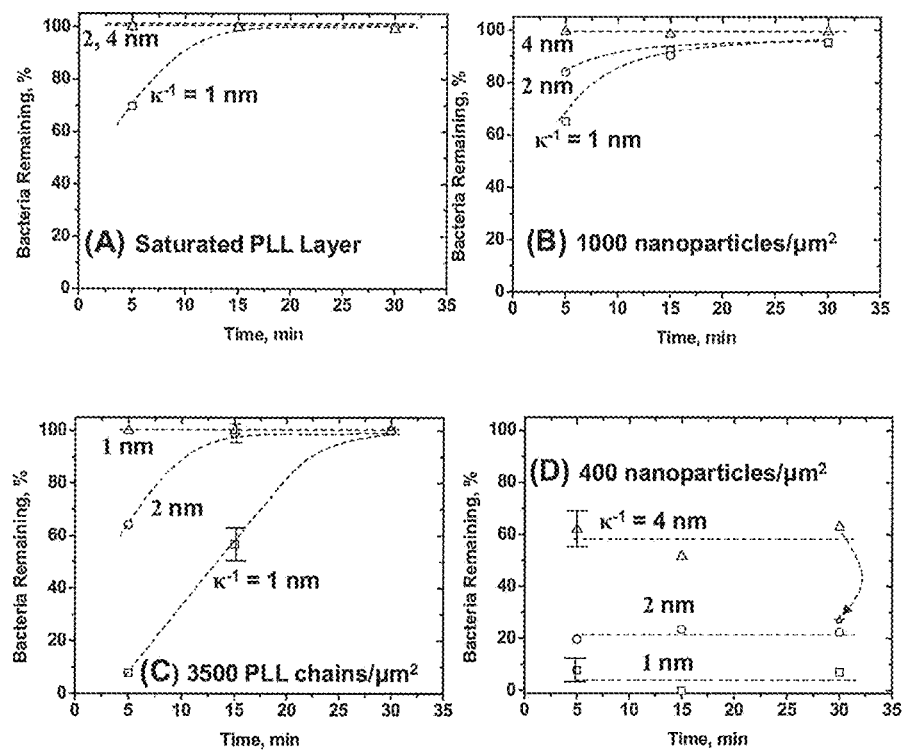
FIGS. 10A to 10D are graphs showing how the incubation time (or residence time) on the surface influences the ease of bacteria removal by elevated shear. The graphs in FIG. 10 show the numbers of bacteria remaining as function of surface residence time (minutes) for: a saturated poly-l-lysine layer (FIG. 10A); a PEG brush containing 1000 cationically-functionalize nanoparticles/μm$^2$ (FIG. 10B); a PEG brush containing 3500 PLL patches/μm$^2$ (FIG. 10C); and a PEG brush containing 400 cationically-functionalized nanoparticles/μm$^2$ (FIG. 10D), in which the symbols represent aging and shear challenge in buffers having different Debye lengths: triangles-4 nm; circles-2 nm; squares-1 nm, and wherein the star in FIG. 10D is for a run aged in 4 mM buffer but challenged in 1 mM buffer and where error bars are shown and dashed lines guide the eye.

FIGS. 10A-10D summarize the sizes of the retained bacterial populations, like those in FIG. 9A, as a function of surface residence time for different surfaces and ionic strengths during the aging period. In FIG. 10A for a saturated layer of PLL, bacterial adhesion immediately exceeds the pull-off-shear force of 12.8 pN, corresponding to shear flow of 1600 s$^{-1}$ past a 1 μm sphere. The results are mostly independent of ionic strength with the exception of the 5-minute aging run in the buffer having $\kappa^{-1}$=1 nm, where a weaker adhesion is found within the first 5 minutes. Within the next 10 minutes, however, the adhesion of these bacteria also grows to the point of maximum pull-off strength in our experiments. In the case of surfaces containing 1000 nanoparticles/μm$^2$ in FIG. 10B, a slight effect of residence time on adhesion was found: Adhesion grows to (and beyond) forces of 12.8 pN in an about 20 minute period, with faster adhesive development at low ionic strength. These observations of strong adhesion are consistent with other reports of strong bacteria-surface adhesion, fast development of bacteria-surface attractions, and the fouling problems on surfaces of relatively uniform cationic functionality.

Different behavior is found for the sparsely cationic surfaces. In the case of 3500 PLL patches/μm$^2$ in FIG. 10C, bacteria subject to aging in buffer having $\kappa^{-1}$=4 nm became strongly adhered (i.e., relatively difficult to remove from the surface) within the first few minutes of capture. At higher ionic strength during aging and shear challenge, the effect of aging time is conspicuous, in that short range electrostatic interactions not only give weaker overall bacterial adhesion, but processes that increase adhesion are slowed when the attraction is made shorter range. This demonstrates that interactions drive the adhesive tightening of bacteria to these surfaces, a process involving evolution of the interfacial structure to increase attractions.

Regarding the adhesion of bacteria on sparsely distributed nanoparticles in FIG. 10D, the development of adhesion is arrested early, and at a level that depends on ionic strength, in that bacteria are more completely removed at high ionic strength. However, the numbers of bacteria that are removed by 12.8 pN force is low and does not grow in time. The "locking in" of low adhesion strength for a substantial time window is a new phenomenon not seen previously and, while not wanting to be bound by theory, attributed to the low level of adhesive functionality and its tightly clustered distribution on the sparse nanoparticle surfaces.

Example 6

This example illustrates the extent of bonding versus strength. Following the protocol of FIG. 9, both the aging of captured bacteria and the shear challenge were conducted at the same ionic strengths. Since the electrostatic interaction at a given time depends on ionic strength, the effect of decoupling the influence of salt on interfacial evolution (aging) from its impact on "bond strength" at the time of shear challenge was investigated. Decoupling the influence of salt on aging from that on bacteria removal involves a switch in buffer just prior to shear challenge, to uniform ionic conditions for bacterial removal (for instance arbitrarily choosing to conduct all shear challenges at a Debye length of 1 nm). Such a protocol was not possible for runs with 5 minute aging times, because about 3 additional minutes are needed to switch to the buffer conditions for shear challenge. The impact of buffer choice during the shear challenge of longer experiments was therefore studied, focusing on the surface and aging conditions where this would be most conspicuous, i.e., a substrate with sparse nanoparticles with bacterial aging in $\kappa^{-1}=4$ nm buffer. Here an additional set of runs involved aging in Debye length 4 nm buffer for 30 minutes and then switching back to 1 nm buffer for the shear challenge, averaged to give the star datum in FIG. 10D.

For a given choice of surface and aging conditions, a lower adhesion strength and fewer retained bacteria following a shear challenge in 1 nm Debye length buffer were expected, compared to that in 4 nm Debye length buffer. This expectation follows from the shorter range of electrostatic interactions during challenge in 1 nm buffer. The expectation is confirmed by the star datum in FIG. 10D compared with the triangle at the same aging time. Importantly, however, the star for aging in 4 nm Debye length buffer lies above the square for aging in 1 nm Debye length buffer (with both shear challenges in 1 nm Debye length buffer conditions). Therefore, this test demonstrates that even when the Debye length is consistently set at low level during shear challenge, the aging rate (increasing adhesion) increases with Debye length during aging. In other words, independent of conditions during shear challenge, the structure of the bacteria-surface interface evolves more rapidly (to strengthen adhesion) in 4 nm Debye length buffer than it does in 1 nm Debye length buffer.

While bacterial adhesion on substantially cationic surfaces rapidly increases to levels exceeding those that can be measured with hydrodynamic pull-off experiments (resisting 12.8 pN within less than 5 minutes of initial capture), distinction between the process of bacterial capture and subsequent increases in adhesion is evident on surfaces with sparse cationic functionality. In the tens of minutes following capture on surfaces containing 3500 PLL patches/$\mu m^2$ in a PEG brush, bacteria become increasingly resistant to removal. On the most sparsely functionalized surfaces (400 nanoparticles/$\mu m^2$), however, adhesion strength remains arrested its low initial level. Any relaxations on the sparse nanoparticle surfaces, therefore, have time constants on the order of hours, exceeding these studies. Without being bound by theory, it is believed that with the sparse PLL surfaces, the influence of ionic strength on the evolution of adhesion after initial capture supports a mechanism of electrostatically-driven "tightening" of the bacteria onto the surface. This adhesive tightening need not involve "living processes" or bacteria metabolism.

The terminology used herein is for the purpose of describing particular embodiments only and is not intended to be limiting. As used herein, the singular forms "a", "an", and "the" are intended to include the plural forms, including "at least one", unless the context clearly indicates otherwise. "Or" means "and/or" unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated can be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this disclosure belongs.

All references cited herein are incorporated by reference herein in their entirety.

While the invention has been described with reference to an exemplary embodiment, it will be understood by those skilled in the art that various changes may be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of capturing and releasing bacteria from an engineered surface, the method comprising:
   providing the engineered surface, wherein the engineered surface comprises
      a substrate,
      biologically or bacterially nonadhesive elements disposed on at least a portion of the substrate, wherein the biologically or bacterially nonadhesive elements comprise polyalkylene glycol, a polyethylene oxide, a polyvinylpyrrolidone, a polyoxazoline, a polyzwitterion, a polyurethane, a polyacrylic, a polyimide polyether ketone, a polyvinyl chloride, or a combination thereof; and
      bacterially adhesive elements disposed on the substrate into nano-scale surface elements that are distributed in a sparse random arrangement, in a pattern; or in nanoscale clusters contacting the biologically or bacterially nonadhesive elements, thereby forming discrete regions of bacterially adhesive functionality, wherein the bacterially adhesive elements are cationic or hydrophobic, have an average largest dimension of about 3 to 100 nm, and wherein the spatial density of the bacterially adhesive elements is 5 elements per square micrometer to 12,000 elements per square micrometer;
   contacting a fluid with the engineered surface under quiescent conditions or in flow at a shear rate up to about 50 $sec^{-1}$, wherein the shear rate of the fluid contacting the engineered surface is selected to capture and adhere at least a portion of the bacteria in the fluid to the engineered surface; and releasing at least a portion of the adhered bacteria from the engineered surface by increasing the shear rate to about 100 sec$^{-1}$ to about 3000 sec-1.

2. The method of claim 1, wherein a Debye length of the fluid is less than or equal to about 4 nm.

3. The method of claim 1, wherein the contacting, selecting the shear rate and releasing are repeated at least a second time.

4. The method of claim 1, wherein the bacterially adhesive elements comprise cationically and/or hydrophobically-functionalized nanoparticles; an inorganic nanoparticle comprising a metal, metal oxide, or a ceramic core; cationically and/or hydrophobically-functionalized gold nanoparticles present at about 100 to 2000 gold nanoparticles per square micrometer, wherein the gold nanoparticles optionally comprise a gold core having an average diameter of about 2 to 20 nm and having about 30 to 2000 ligands disposed thereon; a cationic nanoparticle; a natural or synthetic polymer that is charged, neutral, zwitterionic, or hydrophobic; a cationic synthetic polymer; a cationically-functionalized hydrophobic synthetic polymer; cationically-functionalized hydrophobic synthetic polymer particles; a cationic dendrimer; a polypeptide; a protein; or a combination thereof.

5. The method of claim 4, wherein bacterially adhesive elements comprise a homopolypeptide comprising about 30 to 500 structural units; a polypeptide comprising about 20 to 500 structural units; or poly-l-lysine having a molecular weight of about 10 to 70 kiloDaltons.

6. The method of claim 4, wherein the bacterially adhesive elements comprise cationically and/or hydrophobically-functionalized gold nanoparticles present at about 150, 250 or 400 gold nanoparticles per square micrometer; or amine-functionalized silica nanoparticles.

7. The method of claim 1, wherein the biologically or bacterially nonadhesive elements are crosslinked, grafted, end-grafted, a polymer brush, part of a copolymer, charged, neutral, zwitterionic, solvated, sterically repulsive, or a combination thereof, and when not crosslinked, have a molecular weight of about 0.1 to about 500 kiloDaltons.

8. The method of claim 1, wherein the biologically or bacterially nonadhesive elements on the engineered surface comprise a polyethylene glycol (PEG) brush having surface density of about 1 mg/m$^2$.

9. The method of claim 1, wherein during releasing, the shear rate is progressively increased.

10. The method of claim 1, wherein at least 50% of the adhered bacteria are released from the engineered surface.

11. The method of claim 1, wherein at least 95% of the adhered bacteria are released from the engineered surface.

12. The method of claim 1, wherein at least 50 volume percent of the fluid is water, optionally at least 80 volume percent is water, at least 90 volume percent is water, at least 95 volume percent is water, or at least 99.5 volume percent is water.

13. The method of claim 1, wherein the bacterially adhesive elements are gold nanoparticles having a minimum density of 150 gold-nanoparticles per square micrometer, or wherein the bacterially adhesive elements are poly-l-lysine elements having a minimum density of about 2500 poly-l-lysine adhesive elements per square micrometer.

14. The method of claim 1, wherein the engineered surface is a component of a biomedical device, a purification device, a textile, or a sensor.

15. The method of claim 1, wherein during releasing at least a portion of the adhered bacteria from the engineered surface, further comprising passing one or more gas bubbles over the engineered surface.

16. The method of claim 1, further comprising detecting the bacteria on the engineered surface.

17. The method of claim 1, wherein the engineered surface is a component of a biomedical device, a purification device, a textile, or a sensor.

18. The method of claim 1, wherein upon contacting a fluid with the engineered surface, waiting for a period of about 1 to about 120 minutes before releasing at least a portion of the adhered bacteria from the engineered surface.

19. The method of claim 18, wherein the fluid further comprises a buffer, and while waiting for the period of about 1 to about 120 minutes the buffer is optionally changed to a buffer having a different ionic strength.

20. The method of claim 18, wherein during the waiting period at least a portion of the adhered bacteria are killed.

21. The method of claim 20, wherein the bacterially adhesive elements have cationic functionality.

22. The method of claim 21, wherein the engineered surface has a charge density of about $5 \times 10^{12}$ to $50 \times 10^{12}$ cationic charges per cm$^2$.

23. The method of claim 20, wherein the bacterially adhesive elements are not antimicrobial in free form, or wherein the killing efficiency of bacteria by the engineered surface is greater than the killing efficiency of the bacterially adhesive elements when they are free in a solution.

24. The method of claim 20, wherein at least about 40% of the adhered bacteria are killed within about 30 minutes of interaction with the engineered surface.

25. The method of claim 20, wherein at least about 80% of the adhered bacteria are killed within about 120 minutes of interaction with the engineered surface.

26. The method of claim 20, wherein the shear rate is increased or maintained during the waiting period.

27. The method of claim 20, wherein at least a portion of the killed bacteria are released from the engineered surface.

28. The method of claim 27, wherein during releasing, the shear rate is progressively increased.

29. The method of claim 20, wherein the contacting, selecting the shear rate, waiting, killing and releasing are repeated at least a second time.

30. A method of selectively capturing and releasing bacteria from an engineered surface, the method comprising:
providing the engineered surface, wherein the engineered surface comprises
a substrate,
biologically or bacterially nonadhesive elements disposed on at least a portion of the substrate, wherein the biologically or bacterially nonadhesive elements comprise a polyalkylene glycol, a polyethylene oxide, a polyvinylpyrrolidone, a polyoxazoline, a polyzwitterion, a polyurethane, a polyacrylic, a polyimide polyether ketone, a polyvinyl chloride, or a combination thereof; and
bacterially adhesive elements disposed on the substrate into nano-scale surface elements that are distributed in a sparse random arrangement, in a pattern, or in nanoscale clusters contacting the biologically or bacterially nonadhesive elements, thereby forming discrete regions of bacterially adhesive functionality, wherein the bacterially adhesive elements are cationic or hydrophobic, have an average largest dimension of about 3 to 100 nm, and wherein the spatial density of the bacterially adhesive elements is 5 elements per square micrometer to 12,000 elements per square micrometer; and contacting a fluid with the engineered surface under quiescent conditions or in flow at a shear rate up to about 50 sec$^{-1}$, wherein the shear rate of the fluid contacting the engineered surface is selected to selectively capture and adhere at least a portion of at least a first bacteria type in the fluid to the engineered surface, wherein the fluid comprise another biological component; and releasing at least a portion of the selectively adhered first bacteria type from the engineered surface by increasing the shear rate to about 100 sec$^{-1}$ to about 3000 sec-1.

31. The method of claim 30, wherein a Debye length of the fluid is less than or equal to about 4 nm.

32. The method of claim 30, wherein the selectively capturing the first bacteria type does not rely on an antibody type molecular recognition.

33. The method of claim 30, wherein the another biological component comprises a virus, a mammalian cell, a non-targeted bacteria, a polypeptide, a protein, a nucleic acid, an oligonucleotide, a polynucleotide, a sugar, an oligosaccharide, a carbohydrate, a metabolite, a drug, a fat, a lipid, or a combination thereof.

34. The method of claim 30, wherein the bacterially adhesive elements comprise cationically and/or hydrophobically-functionalized nanoparticles; an inorganic nanoparticle comprising a metal, metal oxide, or a ceramic core; cationically and/or hydrophobically-functionalized gold nanoparticles present at about 100 to 2000 gold nanoparticles per square micrometer, wherein the gold nanoparticles optionally comprise a gold core having an average diameter of about 2 to 20 nm and having about 30 to 2000 ligands disposed thereon; a cationic nanoparticle; a natural or synthetic polymer that is charged, neutral, zwitterionic, or hydrophobic; a cationic synthetic polymer; a cationically-functionalized hydrophobic synthetic polymer; cationically-functionalized hydrophobic synthetic polymer particles; a cationic dendrimer; a polypeptide; a protein; or a combination thereof.

35. The method of claim 34, wherein bacterially adhesive elements comprise a homopolypeptide comprising about 30 to 500 structural units; a polypeptide comprising about 20 to 500 structural units; or poly-l-lysine having a molecular weight of about 10 to about 70 kiloDaltons.

36. The method of claim 34, wherein the bacterially adhesive elements comprise cationically and/or hydrophobically-functionalized gold nanoparticles present at about 150, 250 or 400 gold nanoparticles per square micrometer; or amine-functionalized silica nanoparticles.

37. The method of claim 30, wherein the biologically or bacterially nonadhesive elements are crosslinked, grafted, end-grafted, a polymer brush, part of a copolymer, charged, neutral, zwitterionic, solvated, sterically repulsive, or a combination comprising at least one of the foregoing, and when not crosslinked, have a molecular weight of about 0.1 to about 500 kiloDaltons.

38. The method of claim 30, wherein the biologically or bacterially nonadhesive elements on the engineered surface comprise a polyethylene glycol (PEG) brush having surface density of about 1 mg/m$^2$.

39. The method of claim 30, wherein during releasing, the shear rate is progressively increased.

40. The method of claim 30, wherein at least 50% of the adhered first bacteria type are released from the engineered surface.

41. The method of claim 30, wherein at least 95% of the adhered first bacteria type are released from the engineered surface.

42. The method of claim 30, wherein at least 50 volume percent of the fluid is water, optionally at least 80 volume percent is water, at least 90 volume percent is water, at least 95 volume percent is water, or at least 99.5 volume percent is water.

43. The method of claim 30, wherein during releasing at least a portion of the adhered bacteria from the engineered surface, further comprising passing one or more gas bubbles over the engineered surface.

44. The method of claim 30, further comprising detecting the bacteria on the engineered surface.

45. The method of claim 30, wherein upon contacting a fluid with the engineered surface, waiting for a period of about 1 to about 120 minutes before releasing at least a portion of the adhered bacteria from the engineered surface.

46. The method of claim 45, wherein the contacting, selecting the shear rate, waiting, and releasing are repeated at least a second time.

47. The method of claim 45, wherein the fluid further comprises a buffer, and while waiting for the period of about 1 to about 120 minutes the buffer is optionally changed to a buffer having a different ionic strength.

48. The method of claim 45, wherein during the waiting period at least a portion of the captured first bacteria type is killed.

49. The method of claim 48, wherein at least a portion of the killed first bacteria type is released from the engineered surface.

50. The method of claim 49, wherein during releasing, the shear rate is progressively increased.

51. The method of claim 48, wherein the contacting, selecting the shear rate, waiting, killing and releasing are repeated at least a second time.

52. The method of claim 48, wherein the bacterially adhesive elements have cationic functionality.

53. The method of claim 52, wherein the engineered surface has a charge density of about $5\times10^{12}$ to $50\times10^{12}$ cationic charges per cm$^2$.

54. The method of claim 48, wherein at least about 40% of the adhered bacteria are killed within about 30 minutes of interaction with the engineered surface.

55. The method of claim 48, wherein at least about 80% of the adhered bacteria are killed within about 120 minutes of interaction with the engineered surface.

56. A method of capturing, killing and releasing bacteria from an engineered surface, the method comprising:

providing the engineered surface, wherein the engineered surface comprises a substrate, biologically or bacterially nonadhesive elements disposed on at least a portion of the substrate, wherein the biologically or bacterially nonadhesive elements comprise a polyalkylene glycol, a polyethylene oxide, a polyvinylpyrrolidone, a polyoxazoline, a polyzwitterion, a polyurethane, a polyacrylic, a polyimide polyether ketone, a polyvinyl chloride, or a combination thereof, and bacterially adhesive elements disposed on the substrate into nano-scale surface elements that are distributed in a sparse random arrangement, in a pattern, or in nanoscale clusters contacting the biologically or bacterially nonadhesive elements, thereby forming discrete regions of bacterially adhesive functionality, wherein the bacterially adhesive elements are cationic or hydrophobic and have an average largest dimension of about 3 to 100 nm, and wherein the spatial density of bacterially adhesive elements is 5 elements per square micrometer to 12,000 elements per square micrometer;

contacting a fluid with the engineered surface under quiescent conditions or in flow at a shear rate up to about 50 $sec^{-1}$, wherein the shear rate of the fluid contacting the engineered surface is selected to capture and adhere at least a portion of the bacteria in the fluid to the engineered surface;

waiting for a period of about 1 to about 120 minutes, wherein during the capture and/or waiting period at least a portion of the captured bacteria are killed; and releasing at least a portion of the adhered bacteria from the engineered surface by increasing the shear rate to about 100 $sec^{-1}$ to about 3000 $sec^{-1}$.

* * * * *